US012797469B2

(12) United States Patent
Kaneda et al.

(10) Patent No.: US 12,797,469 B2
(45) Date of Patent: Nov. 17, 2026

(54) METHOD FOR TREATING CANCER AND SYSTEM FOR SAME

(71) Applicants: OTSUKA MEDICAL DEVICES CO., LTD., Tokyo (JP); OTSUKA ELECTRONICS CO., LTD., Hirakata (JP); JIMRO CO., LTD., Takasaki (JP)

(72) Inventors: Kenta Kaneda, Takasaki (JP); Hidetaka Maegawa, Takasaki (JP)

(73) Assignees: OTSUKA MEDICAL DEVICES CO., LTD., Tokyo (JP); OTSUKA ELECTRONICS CO., LTD., Hirakata (JP); JIMRO CO., LTD., Takasaki (JP)

( * ) Notice: Subject to any disclaimer, the term of this patent is extended or adjusted under 35 U.S.C. 154(b) by 1102 days.

(21) Appl. No.: 17/768,769

(22) PCT Filed: Mar. 24, 2021

(86) PCT No.: PCT/JP2021/012318
§ 371 (c)(1),
(2) Date: Apr. 13, 2022

(87) PCT Pub. No.: WO2021/193744
PCT Pub. Date: Sep. 30, 2021

(65) Prior Publication Data
US 2024/0108725 A1 Apr. 4, 2024

(30) Foreign Application Priority Data
Mar. 25, 2020 (WO) .................. PCT/JP2020/013427

(51) Int. Cl.
*A61K 41/00* (2020.01)
*A61K 35/14* (2015.01)
*A61P 35/02* (2006.01)

(52) U.S. Cl.
CPC .......... *A61K 41/0061* (2013.01); *A61K 35/14* (2013.01); *A61P 35/02* (2018.01)

(58) Field of Classification Search
CPC ................ A61K 41/0061; A61K 35/14; A61K 31/197; A61P 35/00; A61M 1/3683
See application file for complete search history.

(56) References Cited

U.S. PATENT DOCUMENTS 8,057,418 B2 11/2011 Korbling et al.
10,695,371 B2 6/2020 Peng et al.
(Continued)

FOREIGN PATENT DOCUMENTS

CN 1802186 A 7/2006
CN 102068723 A 5/2011
(Continued)

OTHER PUBLICATIONS

International Preliminary Report on Patentability with the translation of Written Opinion dated Sep. 22, 2022 from the International Bureau in International Application No. PCT/JP2021/012318.
(Continued)

*Primary Examiner* — San Ming R Hui
(74) *Attorney, Agent, or Firm* — Sughrue Mion, PLLC

(57) ABSTRACT

The present disclosure includes a system for use in the treatment of cancer, the system comprising
- an extracorporeal circulation device comprising a blood circuit and a blood pump to collect and return blood of a subject, and
- a light irradiation device to irradiate the blood circuit with light,
- wherein a photosensitive substance is administered to the subject prior to blood collection, or added to blood collected from the subject prior to light irradiation,
- the blood collected from the subject and irradiated with light is returned to the subject, and (Continued)

the light has an irradiation energy density of 2.5 to 300 $J/cm^2$.

19 Claims, 8 Drawing Sheets

(56) References Cited

U.S. PATENT DOCUMENTS

| | | | |
|---|---|---|---|
| 2006/0282132 | A1 | 12/2006 | Arai et al. |
| 2009/0156976 | A1 | 6/2009 | Korbling et al. |
| 2015/0122738 | A1 | 5/2015 | Kim |
| 2016/0361418 | A1 | 12/2016 | Ishikawa et al. |
| 2017/0042938 | A1 | 2/2017 | Peng |
| 2019/0365927 | A1 | 12/2019 | Choi |

FOREIGN PATENT DOCUMENTS

| | | | |
|---|---|---|---|
| CN | 103732271 | A | 4/2014 |
| CN | 106880881 | A | 6/2017 |
| CN | 110198741 | A | 9/2019 |
| JP | 2010-519955 | A | 6/2010 |
| JP | 2017-513952 | A | 6/2017 |
| WO | 2012/142180 | A1 | 10/2012 |
| WO | 2015/125732 | A1 | 8/2015 |

OTHER PUBLICATIONS

International Preliminary Report on Patentability with the translation of Written Opinion dated Sep. 22, 2022 from the International Bureau in International Application No. PCT/JP2020/013427.
International Search Report dated May 11, 2021, issued in International Application No. PCT/JP2021/012318.
International Search Report dated Jun. 9, 2020, issued in International Application No. PCT/JP 2020/013427.
Gollnick, S.O. et al., "Generation of Effective Antitumor Vaccines Using Photodynamic Therapy", Cancer Research, 2002, vol. 62, pp. 1604-1608 (6 pages).
Moon, Y. H. et al., "Efficient preparation of highly pure chlorin e6 and its photodynamic anti-cancer activity in a rat tumor model", Oncology Reports, 2009, vol. 22, No. 5, pp. 1085-1091 (7 pages).
Castano, A. P. et al., "Anti-tumor immunity generated by photodynamic therapy in a metastatic murine tumor model", Proceedings of SPIE, 2005, vol. 5695, pp. 7-16 (11 pages).
Takeuchi, Y. et al., "Induction of Intensive Tumor Suppression by Antiangiogenic Photodynamic Therapy Using Polycation-Modified Liposomal Photosensitizer", Cancer, 2003, vol. 97, No. 8, pp. 2027-2034 (8 pages).
Kim, G. et al., "Extracorporeal Photo-Immunotherapy for Circulating Tumor Cells", PloS One, 2015, vol. 10, No. 5, pp. 1-9 (9 pages).
Cunderlikova, B. et al., "Modification of extracorporeal photopheresis technology with porphyrin precursors. Comparison between 8-methoxypsoralen and hexaminolevulinate in killing human T-cell lymphoma cell lines in vitro", Biochim. Biophys. Acta., 2014, vol. 1840, No. 9, pp. 2702-2708 (7 pages).
International Preliminary Report on Patentability with the translation of Written dated Opinion Jun. 9, 2022 from the International Bureau in International Application No. PCT/JP2020/013427.
Office Action issued on Nov. 24, 2023 in corresponding Chinese patent application No. 202180018005.5.
Huijuan Yin, et al., "Evaluation of the effects of systemic photodynamic therapy in a rat model of acute myeloid leukemia", Journal of Photochemistry & Photobiology, B: Biology, vol. 153, 2015, pp. 13-19.
Sagar Darvekar, et al., "Selective Killing of Activated T Cells by 5-Aminolevulinic Acid Mediated Photodynamic Effect: Potential Improvement of Extracorporeal Photopheresis", Cancers, vol. 12, No. 377, Feb. 6, 2020, pp. 1-22.
Yasuhisa Sando, et al., "5-aminolevulinic acid-mediated photodynamic therapy can target aggressive adult T cell leukemia/lymphoma resistant to conventional chemotherapy", Scientific Reports, vol. 10, No. 17237, 2020, pp. 1-11.
Extended European Search Report dated Aug. 23, 2024 issued by the European Patent Office in European application No. 21774546.2.
Yishan Wang, "Comprehensive Treatment and Rehabilitation of Tumors", First Edition, University of Electronic Science and Technology of China Press, Dec. 2009, pp. 75-76 (4 pages total).
Gang Chen, et al., "Laser Medical Technology", First Edition, Fudan University, Mar. 31, 2018, pp. 155-156 (4 pages total).
Haiping Yang, et al., "Practical Cosmetic Skin Surgery Technology", Frist Edition, Second Military Medical University Press, Apr. 30, 2006, pp. 150-151 (4 pages total).
Office Action dated Sep. 25, 2024 issued by the State Intellectual Property Office of the P.R. China in Chinese application No. 202180018005.5.

METHOD FOR TREATING CANCER AND SYSTEM FOR SAME

CROSS REFERENCE TO RELATED APPLICATIONS

This application is a National Stage of International Application No. PCT/JP2021/012318 filed Mar. 24, 2021, claiming priority based on WO Patent Application No. PCT/JP2020/013427 filed Mar. 25, 2020.

TECHNICAL FIELD

The present disclosure includes a method for treating cancer, and a system, a method of controlling operation of a system, a pharmaceutical composition, and a method for preparing blood for the treatment.

BACKGROUND

Cancer immunotherapy has been attracting attention in recent years as the fourth therapy following surgery, radiation therapy, and pharmacotherapy. Cancer immunotherapy activates immune function of patients, and it can be either a treatment that strengthens anti-cancer immunity or that restores immunity which has been braked by cancer. Cancer immunotherapy has been known to include immune checkpoint inhibitors, CAR-T therapy, cytokine therapy, immunostimulatory agents, cancer vaccine therapy, and dendritic cell therapy.

Photodynamic therapy (PDT) is a therapy that utilizes a photochemical reaction of a photosensitive substance and light irradiation, and has been put to practical use in the treatment of lung cancer or esophageal cancer. In the cancer treatment with PDT, a systemically administered photosensitive substance accumulates in cancer cells, and thereby can damage cancer without affecting normal tissues. Currently, PDT has not been used clinically to activate immune function of patients.

SUMMARY

Problems to be Solved

An object of the present disclosure is to provide a method for treating cancer, and a system, a method of controlling operation of a system, a pharmaceutical composition, and a method for preparing blood for the treatment.

Means to Solve Problems

In an aspect, the present disclosure provides a system for use in the treatment of cancer, the system comprising an extracorporeal circulation device comprising a blood circuit and a blood pump to collect and return blood of a subject, and a light irradiation device to irradiate the blood circuit with light, wherein a photosensitive substance is administered to the subject prior to blood collection, or added to blood collected from the subject prior to light irradiation, the blood collected from the subject and irradiated with light is returned to the subject, and the light has an irradiation energy density of 2.5 to 300 $J/cm^2$.

In a further aspect, the present disclosure provides a method of controlling operation of a system for use in the treatment of cancer, the system comprising an extracorporeal circulation device comprising a blood circuit and a blood pump to collect and return blood of a subject, and a light irradiation device to irradiate the blood circuit with light, wherein a photosensitive substance has been administered to the subject prior to blood collection, or added to blood collected from the subject prior to light irradiation, the method comprising controlling operation of the system so that the light irradiation device emits light having an irradiation energy density of 2.5 to 300 $J/cm^2$.

In a further aspect, the present disclosure provides a pharmaceutical composition for use in the treatment of cancer comprising a photosensitive substance, wherein the pharmaceutical composition is for use in a method comprising (1) irradiating blood collected from a subject with light, and (2) returning the light-irradiated blood to a vein of the subject, wherein the photosensitive substance is administered to the subject prior to blood collection, or added to the blood collected from the subject prior to light irradiation, and the light has an irradiation energy density of 2.5 to 300 $J/cm^2$.

In a further aspect, the present disclosure provides a method for treating cancer, the method comprising (1) irradiating blood collected from a subject with light, and (2) returning the light-irradiated blood to a vein of the subject, wherein a photosensitive substance is administered to the subject prior to blood collection, or added to the blood collected from the subject prior to light irradiation, and the light has an irradiation energy density of 2.5 to 300 $J/cm^2$.

In a further aspect, the present disclosure provides a method of preparing blood for use in the treatment of cancer, the method comprising adding a photosensitive substance to blood collected from a subject, and irradiating the blood to which the photosensitive substance is added with light, wherein the light-irradiated blood is to be administered to a vein of the subject, and the light has an irradiation energy density of 2.5 to 300 $J/cm^2$.

Effects of Invention

The present disclosure provides an effective method for treating cancer, and a system, a method of controlling operation of a system, a pharmaceutical composition, and a method for preparing blood for the treatment.

DETAILED DESCRIPTION OF EMBODIMENTS

Figure 1:
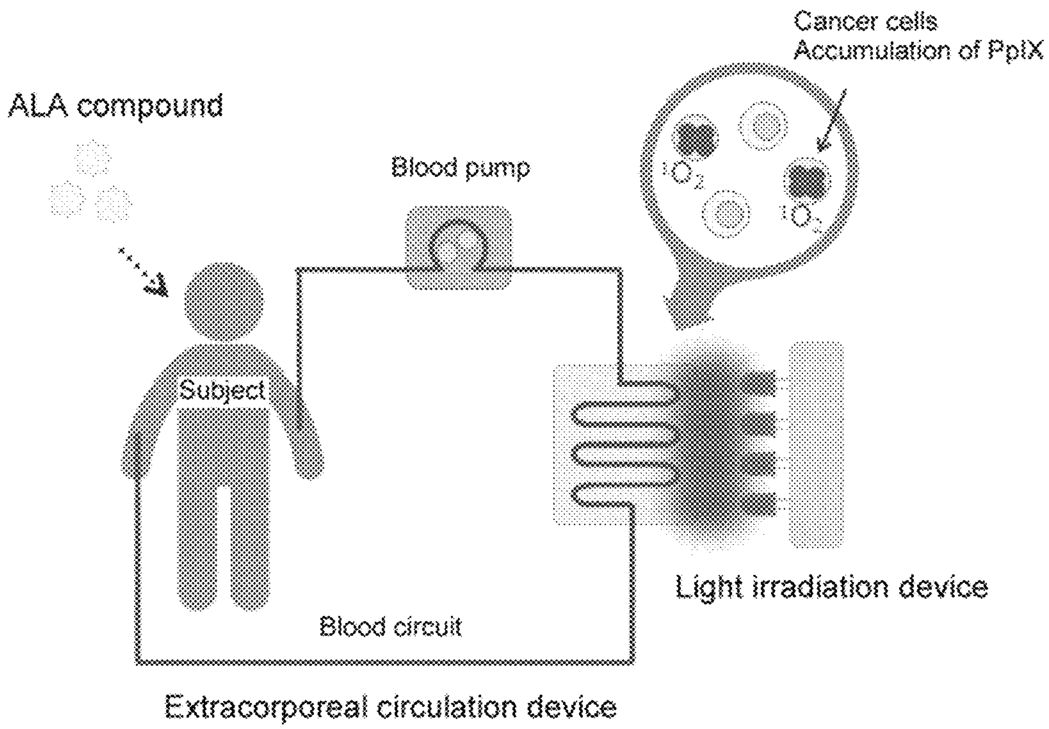
FIG. 1 is an explanatory scheme of an embodiment of the present disclosure.

Unless otherwise specified, the terms used herein have the meanings generally understood by those skilled in the art in the fields such as organic chemistry, medical science, pharmaceutical science, molecular biology, and microbiology. The followings are definitions of some terms used herein, which supersede general understandings in the present disclosure.

In the present disclosure, when a number is accompanied by the term "about", it is intended to include a range of ±10% of that value. For example, "about 20" shall include "18 to 22". The range of numbers includes all numbers between the endpoints and the numbers at the endpoints. The "about" for a range applies to both ends of the range. Therefore, for example, "about 20 to 30" shall include "18 to 33".

In the present disclosure, cancer is treated by using PDT with a photosensitive substance. It has been known that cancer cells exist and circulate in the peripheral blood of cancer patients not only in blood cancer patients but also in solid cancer patients. When cancer cells in the blood are carried to an organ other than the primary lesion by the bloodstream and settle therein, a metastatic lesion develops. When blood collected from a subject to which a photosensitive substance has been administered is irradiated with light, or blood which has been collected from a subject and to which a photosensitive substance has been added is irradiated with light, cancer cells in the blood are damaged. When the blood containing the damaged cancer cells is returned to the subject, immune response is enhanced in the subject and cancer cells in the subject's body are damaged. Thus, the cancer is treated as a result of direct damage of cancer cells by light irradiation and enhancement of immune response in the subject.

Enhancement of immune response in a subject makes it possible to damage not only cancer cells in the light-irradiated blood, but also cancer cells in any part of the subject's body, including cancer cells in the primary lesion and a metastatic lesion, and then prevent cancer metastasis. In the present disclosure, treatment of cancer includes treatment of a lesion in the peripheral blood, lymph node, spleen, liver or any other extranodal organ (e.g., lung, central nerve, bone, or gastrointestinal tract), skin, or bone marrow. Further, in the present disclosure, treatment of cancer includes treatment of the primary lesion, treatment of a metastatic lesion (herein also referred to as treatment of cancer metastasis), and prevention of development of a metastatic lesion (herein also referred to as prevention of cancer metastasis). In an embodiment, cancer metastasis is prevented or treated. The cancer metastasis includes a lesion of the peripheral blood, lymph node, spleen, liver or any other extranodal organ (e.g., lung, central nerve, bone, or gastrointestinal tract), skin, or bone marrow. In a further embodiment, the cancer metastasis is a skin lesion (e.g., a skin lesion of a blood cancer).

The cancer in the present disclosure is not limited to, but may be a blood cancer or a solid cancer, and may be a primary cancer or a metastatic cancer. Examples of cancer include adult T-cell leukemia (ATL), acute myeloid leukemia (AML), acute lymphocytic leukemia (ALL), chronic myeloid leukemia (CML), chronic lymphocytic leukemia (CLL), gastric cancer, lung cancer, colorectal cancer, pancreatic cancer, liver cancer (hepatic cell cancer, intrahepatic bile duct cancer), kidney cancer, breast cancer, uterine cancer, cervical cancer, ovarian cancer, prostate cancer, osteosarcoma, chondrosarcoma, rhabdomyosarcoma, leiomyosarcoma, fibrosarcoma, liposarcoma, and angiosarcoma. In an embodiment, the cancer is a blood cancer such as ATL, AML, ALL, CML, or CLL. In a further embodiment, the blood cancer is ATL. The treatment of ATL includes treatment of a lesion in the peripheral blood, lymph node, spleen, liver or any other extranodal organ (e.g., lung, central nerve, bone, or gastrointestinal tract), skin, or bone marrow.

As used herein, a photosensitive substance means a substance that exerts its pharmacological effect after light irradiation, and the term is used in the sense that it also includes a precursor that produces such a substance intracellularly. Examples of photosensitive substances include, but are not limited to, psoralen, porphyrin, and phthalocyanine and their derivatives such as ALA compounds, talaporfin sodium, IR700, porfimer sodium, verteporfin, temoporfin, padeliporfin, tetra(metahydroxyphenyl)chlorin (mTHPC), 2-(1-hexyloxyethyl)-2-devinylpyro pheophorbide-a (HPPH), tin ethyl etiopurpurin (SnET2), and hypericin. In the above, the "derivative" means a substance that is structurally related to the original substance and has a property as a photosensitive substance. As used herein, the expression "capable of activating a photosensitive substance" means that it can make the photosensitive substance possible to exert its pharmacological effect.

In an embodiment, the photosensitive substance is an ALA compound. As used herein, the term ALA compound means 5-aminolevulinic acid (5-ALA) or an ester thereof or a pharmaceutically acceptable salt thereof. The ALA compound is intracellularly converted to protoporphyrin IX (herein also referred to as PpIX), which selectively accumulates in cancer cells. When PpIX is activated by light irradiation, singlet oxygen is generated and cancer cells are damaged.

Examples of 5-ALA esters include 5-ALA-methyl ester (methyl aminolevulinate), 5-ALA-ethyl ester, 5-ALA-propyl ester, and 5-ALA-hexyl ester (hexaminolevulinate; HAL), 5-ALA-heptyl ester, and 5-ALA-octyl ester. In an embodiment, the ALA compound is 5-ALA, a methyl or hexyl ester thereof, or a pharmaceutically acceptable salt thereof. Examples of pharmaceutically acceptable salts include salts with inorganic acids (e.g., hydrochloric acid, hydrobromic acid, phosphoric acid, and sulfuric acid) or organic acids (e.g., trifluoroacetic acid, propionic acid, maleic acid, fumaric acid, malic acid, citric acid, tartaric acid, lactic acid, benzoic acid, methanesulfonic acid, ethanesulfonic acid, benzenesulfonic acid, toluenesulfonic acid and naphthalenedisulfonic acid). In an embodiment, the pharmaceutically acceptable salt is a hydrochloride or phosphate.

The photosensitive substance may form a complex with any other substance. In an embodiment, the photosensitive substance forms a complex with an antibody directed to cancer cells. The antibody directed to cancer cells can be an antibody against a tumor antigen. The antibody directed to cancer cells is not limited to, but may be an antibody against, EGFR, PSMA, CEA, CD19, CD20, CD22, CD30, CD33, CD38, CD52, CD147, HER2, VEGF, VEGFR2, CCR4, PD-1, PD-L1, SLAMF7, CTLA4, EpCAM, or PAP2a.

In an embodiment, a photosensitive substance is administered to a subject prior to blood collection. For example, a photosensitive substance may administered to a subject 2 to 48 hours, 2 to 12 hours, 2 to 10 hours, 2 to 8 hours, 2 to 6 hours, 2 to 4 hours, or 4 to 6 hours before blood collection from the subject.

A photosensitive substance can be administered to a subject by oral administration or by parenteral administration such as intravenous, transdermal, or rectal administration. In an embodiment, the photosensitive substance is administered by oral administration or by intravenous administration. In a further embodiment, the photosensitive substance is administered by oral administration.

A photosensitive substance is administered at a dose appropriately adjusted based on factors such as age and disease of the subject, the photosensitive substance to be used, and irradiation energy density of the light. For example, in the case of humans, a photosensitive substance can be administered at 1 mg to 100 mg/kg, 1 mg to 80 mg/kg, 1 mg to 60 mg/kg, 1 mg to 50 mg/kg, 1 mg to 40 mg/kg, 1 mg to 30 mg/kg, 10 mg to 60 mg/kg, 10 mg to 50 mg/kg, 10 mg to 40 mg/kg, 10 mg to 30 mg/kg, 20 mg to 60 mg/kg, 20 mg to 50 mg/kg, 20 mg to 40 mg/kg, 20 mg to 30 mg/kg, or about 20 mg/kg.

In a different embodiment, a photosensitive substance is added to blood collected from a subject prior to light irradiation. For example, a photosensitive substance is added to the blood 1 hour to 48 hours, 2 hours to 24 hours, or 4 hours to 24 hours before light irradiation, e.g., 2 hours, 4 hours, 6 hours, 8 hours, 10 hours, 12 hours, or 24 hours before light irradiation. The photosensitive substance is added in an amount appropriately adjusted based on factors such as age and disease of the subject, the photosensitive substance to be used, and irradiation energy density of the light. For example, in the case of humans, a photosensitive substance may be added at 0.001 mg to 1 mg/mL, 0.003 mg to 0.3 mg/mL, or 0.01 mg to 0.3 mg/mL, or 0.01 mmol to 10 mmol/L, 0.03 mmol to 3 mmol/L, 0.03 mmol to 1 mmol/L, 0.1 mmol to 1 mmol/L, 0.25 mmol to 1 mmol/L, 0.3 mmol to 1 mmol/L, or 0.5 mmol to 1 mmol/L.

In a preferred embodiment, a photosensitive substance is administered to a subject prior to blood collection.

In the present disclosure, the subject can be a human or a non-human mammal, but preferably a human. Examples of subjects include a subject suffering from cancer and a subject at risk of cancer recurrence, especially a subject suffering from ATL and a subject at risk of recurrence of ATL.

In the present disclosure, blood of a subject is collected from a vein and returned (or administered) to a vein.

The blood of a subject can be collected and returned by an extracorporeal circulation device comprising a blood circuit and a blood pump. The blood circuit is usually connected to a peripheral vein of the subject. The blood circuit and blood pump can be those commonly used for extracorporeal circulation of blood. The configuration of the blood circuit is not limited as long as extracorporeal circulation is possible, and in addition to a tube through which the blood flows, it may include any other element such as a blood bag or a device for separation of blood components. If a photosensitive substance is added to blood collected from a subject, it may be added at any part of the blood circuit, and can be added to, for example, blood in a blood bag. In a preferred embodiment, a photosensitive substance is administered to a subject prior to blood collection by an extracorporeal circulation device. The blood circuit may be made of any material as long as the portion irradiated with light allows the blood inside that portion to receive light capable of activating the photosensitive substance. In an example, a tube or a blood bag in the blood circuit is irradiated with light. The length of the tube or the size of the blood bag irradiated with light and/or the flow velocity of the blood can be adjusted so that the total irradiation duration of the light to the blood become a desired duration. The light may be irradiated to a part of the collected blood (for example, a leukocyte fraction) or whole blood, but preferably whole blood.

The duration of extracorporeal circulation is not limited to, but may be, 1 to 3 hours.

The blood of a subject can be collected and returned without using an extracorporeal circulation device. For example, the blood can be collected and returned by using a conventional blood collection or return tools, such as a blood bag equipped with a syringe or needle (and optionally a blood pump). In this embodiment, a photosensitive substance may be administered to the subject or added to blood collected from the subject, but it is preferably added to blood collected from the subject.

The light irradiation device is not particularly limited as long as it includes a light source that generates light capable of activating a photosensitive substance. Examples of light sources include lamps such as a metal halide lamp (Na—Li lamp) in which sodium and lithium are enclosed, a xenon lamp, and a halogen lamp, an LED, lasers such as an excimer dye laser, a semiconductor laser, and a He—Ne laser. In an embodiment, the light source is an LED.

The light has a wavelength capable of activating a photosensitive substance. The light may be ultraviolet light, visible light, or infrared light. In an embodiment, the light has a wavelength of 200 to 2500 nm. In a further embodiment, the light has a wavelength of 600 to 800 nm, 600 to 700 nm, or about 630 nm.

When the light-irradiated blood is returned to the subject, dead cancer cells contained in the blood are recognized by the immune system of the subject, and immune response to cancer cells in the subject is enhanced. Thus, the light is emitted at a level at which returning the blood collected from the subject and irradiated with the light to the subject enhances immune response to cancer cells in the subject, in other words, the light-irradiated blood functions as a vaccine. The level at which the returning enhances immune response to cancer cells in the subject is a level at which cancer cells in the subject's body other than the cancer cells irradiated with light can be damaged.

In an embodiment, the light is emitted at a level at which proportion of dead cells in cancer cells contained in the blood collected from the subject increases after the light-irradiated blood is returned to the subject. The dead cells can be apoptotic cells and/or necrotic cells. Cancer cells can be determined by detecting a photosensitive substance (e.g., PpIX) accumulated in the cells. Living cells, apoptotic cells, and necrotic cells can be determined, for example, by staining the cells with Annexin V and Propidium Iodide (PI). When the cells are stained with Annexin V and PI, Annexin V (−) and PI (−) cells are determined to be living cells, Annexin V (+) and PI (−) cells are determined to be apoptotic cells, and Annexin V (+) and PI (+) cells are determined to be necrotic cells. The staining with Annexin V and PI can be performed with a commercially available kit such as the FITC Annexin V Apoptosis Detection Kit I (BD).

In one embodiment, in the light-irradiated cancer cells, proportion of living cells immediately after irradiation is 8% or more, and proportion of living cells 24 hours after irradiation is 2% or more lower than that immediately after irradiation. In a further embodiment, in the light-irradiated cancer cells, proportion of living cells immediately after irradiation is 8% or more, proportion of living cells 24 hours after irradiation is 2% or more lower than that immediately after irradiation, and proportion of apoptotic cells or necrotic cells 24 hours after irradiation is 2% or more higher than that immediately after irradiation. As used herein, immediately after irradiation means within 30 minutes from irradiation.

For example, in the light-irradiated cancer cells, the proportion of living cells immediately after irradiation may be 8%, 10%, 15%, 20%, 30%, 40%, 50%, 60%, 70%, 80%, or 90% or more, and the proportion of living cells 24 hours after irradiation is 2%, 5%, 10%, 20%, 30%, 40%, 50%, 60%, 70%, 80%, or 90% or more lower than that immediately after irradiation. Also, for example, in the light-irradiated cancer cells, the proportion of apoptotic cells or necrotic cells 24 hours after irradiation may be 2%, 5%, 10%, 20%, 30%, 40%, 50%, 60%, 70%, 80%, or 90% or more higher than that immediately after irradiation.

In one embodiment, in the light-irradiated cancer cells, the proportion of living cells immediately after irradiation is 20% or more, and the proportion of living cells 24 hours after irradiation is 10% or more lower than that immediately after irradiation. In a further embodiment, in the light-irradiated cancer cells, the proportion of living cells immediately after irradiation is 20% or more, and the proportion of living cells 24 hours after irradiation is 10% or more lower than that immediately after irradiation, and the proportion of apoptotic cells or necrotic cells 24 hours after irradiation is 10% or more higher than that immediately after irradiation.

At a time point at which the light-irradiated blood is returned to the subject, the proportion of living cells in the light-irradiated cancer cells can be 8% or more. For example, at a time point at which the light-irradiated blood is returned to the subject, the proportion of living cells in the light-irradiated cancer cells is 8%, 10%, 15%, 20%, 30%, 40%, 50%, 60%, 70%, 80%, or 90% or more. In an embodiment, at a time point at which the light-irradiated blood is returned to the subject, the proportion of living cells in the light-irradiated cancer cells is 20% or more.

In an embodiment, the light is emitted at a level at which the amount of singlet oxygen generated in the blood collected from the subject as a result of light irradiation is less than $0.32\times10^{-3}$ mol/L, or less than $10^9$ singlet oxygen molecules/cell.

In an embodiment, the light is emitted at illuminance and duration to have an irradiation energy density of 0.1 J/cm$^2$, 0.5 J/cm$^2$, 1 J/cm$^2$, 1.5 J/cm$^2$, 2 J/cm$^2$, 2.5 J/cm$^2$, 3 J/cm$^2$, 5 J/cm$^2$, 7.5 J/cm$^2$, 10 J/cm$^2$, 20 J/cm$^2$, 30 J/cm$^2$, 40 J/cm$^2$, 50 J/cm$^2$, or 100 J/cm$^2$ or more, and 1000 J/cm$^2$, 500 J/cm$^2$, 400 J/cm$^2$, 350 J/cm$^2$, 300 J/cm$^2$, 250 J/cm$^2$ or 200 J/cm$^2$ or less. In an embodiment, the irradiation energy density is 1 to 300 J/cm$^2$, 2.5 to 300 J/cm$^2$, 5 to 300 J/cm$^2$, or 10 to 300 J/cm$^2$. The irradiation energy density may be 10 to 300 J/cm$^2$, 50 to 300 J/cm$^2$, 100 to 300 J/cm$^2$, 100 to 200 J/cm$^2$ or about 100 J/cm$^2$. The irradiation energy density (J/cm$^2$) is calculated according to the formula: illuminance (W/cm$^2$)× total irradiation duration (second).

The illuminance can be 1 to 300 mW/cm$^2$, 50 to 300 mW/cm$^2$, 100 to 300 mW/cm$^2$, or 150 to 300 mW/cm$^2$. The irradiation may be continuous irradiation or intermittent irradiation, and the total irradiation duration may be, for example, 10 seconds to 30 minutes, 30 seconds to 15 minutes, 1 minute to 10 minutes, or 5 minutes to 10 minutes.

In an embodiment, the photosensitive substance is 5-ALA, and it is administered to a subject at 10 to 60 mg/kg or 20 to 60 mg/kg (e.g., 10, 20, 30, 40, 50 or 60 mg/kg), and the blood collected from the subject is irradiated with light having an irradiation energy density of 10 to 300 J/cm$^2$.

The light may have an irradiation energy density at which proportion of living cells 24 hours after irradiation is lower than that immediately after irradiation in the test described in Example 3. In one embodiment, the light has an irradiation energy density at which proportion of living cells in a cell suspension irradiated with the light 24 hours after irradiation is lower than that immediately after irradiation, wherein the cell suspension is prepared by culturing cancer cells in a medium containing 0.5 mM 5-ALA for 4 hours, collecting the cancer cells, and suspending the collected cells with an erythrocyte solution to provide a cell suspension of $2\times10^7$ cells/mL. The erythrocyte solution means a solution containing erythrocytes and phosphate buffered saline (PBS) at a ratio of 45:55. The culturing is performed at 37° C. under 5% $CO_2$ environment. The medium may be any cell culture medium as long as it is suitable for the cancer cells, and may be, for example, 2.5% FBS-containing F-12K medium or 10% FBS-containing RPMI1640 medium. The cancer cells are preferably C6 cells or TL-0 ml cells. The wavelength of light is preferably 630 nm. The erythrocytes are hemolyzed after light irradiation before measurement of proportion of living cells (usually within 30 minutes). The hemolysis of erythrocytes can be performed by any conventional process, for example by using an ammonium chloride solution. For example, the light may have an irradiation energy density at which proportion of living cells immediately after irradiation is 8% or more, and proportion of living cells 24 hours after irradiation is 2% or more lower than that immediately after irradiation. Alternatively, the light may have an irradiation energy density at which proportion of living cells immediately after irradiation is 8% or more, and proportion of living cells 24 hours after irradiation is 2% or more lower than that immediately after irradiation, and proportion of apoptotic or necrotic cells 24 hours after irradiation is 2% or more higher than proportion of apoptotic cells or necrotic cells immediately after irradiation. The proportion of living cells immediately after irradiation may be 8%, 10%, 15%, 20%, 30%, 40%, 50%, 60%, 70%, 80%, or 90% or more, and the proportion of living cells 24 hours after irradiation may be 2%, 5%, 10%, 20%, 30%, 40%, 50%, 60%, 70%, 80%, or 90% or more lower than the proportion of living cells immediately after irradiation. The proportion of apoptotic cells or necrotic cells 24 hours after irradiation may be 2%, 5%, 10%, 20%, 30%, 40%, 50%, 60%, 70%, 80%, or 90% or more higher than the proportion of apoptotic cells or necrotic cells immediately after irradiation.

The light-irradiated blood can enhance immune response in the subject to treat cancer. Therefore, the present disclosure includes a method of preparing blood for use in the treatment of cancer.

A pharmaceutical composition comprising a photosensitive substance may comprise a pharmaceutically acceptable carrier and/or an additive in addition to the photosensitive substance as an active ingredient. Examples of pharmaceutically acceptable carriers include sterile water, saline, propylene glycol, polyethylene glycol, vegetable oil, lactose, mannitol, crystalline cellulose, hydroxypropyl cellulose, corn starch, and hydroxypropyl methyl cellulose. Examples of additives include a disintegrant, a stabilizer, an antioxidant, a buffer, a preservative, a surfactant, a chelating agent, a binder, and a lubricant. The dosage form can be, but not limited to, a tablet, capsule, powder, granule, liquid, suspension, injection, or suppository. The pharmaceutical composition can be formulated by any conventional method.

The cancer treatment in the present disclosure may be used in combination with any other anti-cancer agent. Examples of anti-cancer agents include vincristine, cyclophosphamide, doxorubicin, prednisolone, ranimustine, vindesine, etoposide, carboplatin, cytarabine, methotrexate, oxaliplatin, cisplatin, dacarbazine, melphalan, ifosphamide, fluorouracil, vinorelbine, idarubicin, epirubicin, gemcitabine, capecitabine, tegafur, gimeracil, and oteracil potassium (TS-1), paclitaxel, docetaxel, bevacizumab, erlotinib, gefitinib, trastuzumab, interferon α, tamoxifen, irinotecan and a combination of one or more of them.

Exemplary embodiments of the present disclosure are provided below.

[1] A system for use in the treatment of cancer, the system comprising
- an extracorporeal circulation device comprising a blood circuit and a blood pump to collect and return blood of a subject, and
- a light irradiation device to irradiate the blood circuit with light,
- wherein a photosensitive substance is administered to the subject prior to blood collection, or added to blood collected from the subject prior to light irradiation, and
- the system enhances immune response to cancer cells in the subject by returning the blood collected from the subject and irradiated with light to the subject.

[2] The system according to item 1, wherein the light has a level at which proportion of dead cells in cancer cells contained in the blood collected from the subject increases after the blood is returned to the subject.

[3] A system for use in the treatment of cancer, the system comprising
- an extracorporeal circulation device comprising a blood circuit and a blood pump to collect and return blood of a subject, and
- a light irradiation device to irradiate the blood circuit with light,
- wherein a photosensitive substance is administered to the subject prior to blood collection, or added to blood collected from the subject prior to light irradiation,
- the blood collected from the subject and irradiated with light is returned to the subject, and
- the light has a level at which proportion of dead cells in cancer cells contained in the blood collected from the subject increases after the blood is returned to the subject.

[4] The system according to any one of items 1 to 3, wherein the light has an irradiation energy density of 2.5 to 300 J/cm$^2$.

[5] A system for use in the treatment of cancer, the system comprising
- an extracorporeal circulation device comprising a blood circuit and a blood pump to collect and return blood of a subject, and
- a light irradiation device to irradiate the blood circuit with light,
- wherein a photosensitive substance is administered to the subject prior to blood collection, or added to blood collected from the subject prior to light irradiation,
- the blood collected from the subject and irradiated with light is returned to the subject, and
- the light has an irradiation energy density of 2.5 to 300 J/cm$^2$.

[6] The system according to any one of items 3 to 5, wherein the system enhances immune response to cancer cells in the subject by returning the blood collected from the subject and irradiated with the light to the subject.

[7] The system according to any one of items 1 to 6, wherein the photosensitive substance is administered to the subject prior to blood collection.

[8] The system according to any one of items 1 to 7, further comprising the photosensitive substance.

[9] The system according to any one of items 1 to 8, wherein the light has a wavelength of 200 to 2500 nm.

[10] The system according to item 9, wherein the light has a wavelength of 600 to 800 nm.

[11] The system according to any one of items 1 to 10, wherein the light has an irradiation energy density of 10 to 300 J/cm$^2$.

[12] The system according to item 11, wherein the light has an irradiation energy density of about 100 J/cm$^2$.

[13] The system according to any one of items 1 to 12, wherein the photosensitive substance is an ALA compound.

[14] The system according to item 13, wherein the ALA compound is 5-aminolevulinic acid (5-ALA), a methyl ester or hexyl ester thereof, or a pharmaceutically acceptable salt thereof.

[15] The system according to item 14, wherein the ALA compound is 5-ALA or a pharmaceutically acceptable salt thereof.

[16] The system according to item 15, wherein 5-ALA or a pharmaceutically acceptable salt thereof is administered to the subject at a dose of 1 mg to 100 mg/kg.

[17] The system according to item 15, wherein 5-ALA or a pharmaceutically acceptable salt thereof is added to the blood collected from the subject at 0.01 mmol to 10 mmol/L.

[18] The system according to any one of items 1 to 17, wherein the cancer is a blood cancer.

[19] The system according to item 18, wherein the blood cancer is adult T-cell leukemia (ATL), acute myeloid leukemia (AML), acute lymphocytic leukemia (ALL), chronic myeloid leukemia (CML), or chronic lymphocytic leukemia (CLL).

[20] The system according to item 19, wherein the blood cancer is ATL.

[21] The system according to any one of items 1 to 17, wherein the cancer is a solid cancer.

[22] The system according to any of items 1 to 21, wherein the system is for use in the treatment of a lesion of peripheral blood, lymph node, spleen, liver or any other extranodal organ, skin, or bone marrow.

[23] The system according to any one of items 1 to 21, wherein the system is for use in the prevention or treatment of cancer metastasis.

[24] The system according to item 23, wherein the cancer metastasis is a lesion of peripheral blood, lymph node, spleen, liver or any other extranodal organ, skin, or bone marrow.

[25] A method of controlling operation of a system for use in the treatment of cancer,
the system comprising
an extracorporeal circulation device comprising a blood circuit and a blood pump to collect and return blood of a subject, and
a light irradiation device to irradiate the blood circuit with light,
wherein a photosensitive substance has been administered to the subject prior to blood collection, or added to blood collected from the subject prior to light irradiation,
the method comprising controlling operation of the system so that the light irradiation device emits light having a level at which returning the blood collected from the subject and irradiated with the light to the subject enhances immune response to cancer cells in the subject.

[26] The method according to item 25, wherein the light has a level at which proportion of dead cells in cancer cells contained in the blood collected from the subject increases after the blood is returned to the subject.

[27] A method of controlling operation of a system for use in the treatment of cancer,
the system comprising
an extracorporeal circulation device comprising a blood circuit and a blood pump to collect and return blood of a subject, and
a light irradiation device to irradiate the blood circuit with light,
wherein a photosensitive substance has been administered to the subject prior to blood collection, or added to blood collected from the subject prior to light irradiation,
the method comprising controlling operation of the system so that the light irradiation device emits light having a level at which proportion of dead cells in cancer cells contained in the blood collected from the subject increases after the blood is returned to the subject.

[28] The method according to any one of items 25 to 27, wherein the light has an irradiation energy density of 2.5 to 300 J/cm$^2$.

[29] A method of controlling operation of a system for use in the treatment of cancer,
the system comprising
an extracorporeal circulation device comprising a blood circuit and a blood pump to collect and return blood of a subject, and
a light irradiation device to irradiate the blood circuit with light,
wherein a photosensitive substance has been administered to the subject prior to blood collection, or added to blood collected from the subject prior to light irradiation,
the method comprising controlling operation of the system so that the light irradiation device emits light having an irradiation energy density of 2.5 to 300 J/cm$^2$.

[30] The method according to any one of items 27 to 29, wherein the light has a level at which returning the blood collected from the subject and irradiated with the light to the subject enhances immune response to cancer cells in the subject.

[31] The method according to any one of items 25 to 30, wherein the photosensitive substance has been administered to the subject prior to blood collection.

[32] The method according to any one of items 25 to 31, wherein the light emitted from the light irradiation device has a wavelength of 200 to 2500 nm.

[33] The method according to item 32, wherein the light emitted from the light irradiation device has a wavelength of 600 to 800 nm.

[34] The method according to any one of items 25 to 33, wherein the light emitted from the light irradiation device has an irradiation energy density of 10 to 300 J/cm$^2$.

[35] The method according to item 34, wherein the light emitted from the light irradiation device has an irradiation energy density of about 100 J/cm$^2$.

[36] The method according to any one of items 25 to 35, wherein the photosensitive substance is an ALA compound.

[37] The method according to item 36, wherein the ALA compound is 5-aminolevulinic acid (5-ALA), a methyl ester or hexyl ester thereof, or a pharmaceutically acceptable salt thereof.

[38] The method according to item 37, wherein the ALA compound is 5-ALA or a pharmaceutically acceptable salt thereof.

[39] The method according to item 38, wherein 5-ALA or a pharmaceutically acceptable salt thereof has been administered to the subject at a dose of 1 mg to 100 mg/kg.

[40] The method according to item 38, wherein 5-ALA or a pharmaceutically acceptable salt thereof has been added to the blood collected from the subject at 0.01 mmol to 10 mmol/L.

[41] The method according to any one of items 25 to 40, wherein the cancer is a blood cancer.

[42] The method according to item 41, wherein the blood cancer is adult T-cell leukemia (ATL), acute myeloid leukemia (AML), acute lymphocytic leukemia (ALL), chronic myeloid leukemia (CML), or chronic lymphocytic leukemia (CLL).

[43] The method according to item 42, wherein the blood cancer is ATL.

[44] The method according to any one of items 25 to 40, wherein the cancer is a solid cancer.

[45] The method according to any one of items 25 to 44, wherein the system is for use in the treatment of a lesion of peripheral blood, lymph node, spleen, liver or any other extranodal organ, skin, or bone marrow.

[46] The method according to any one of items 25 to 44, wherein the system is for use in the prevention or treatment of cancer metastasis.

[47] The method according to item 46, wherein the cancer metastasis is a lesion of peripheral blood, lymph node, spleen, liver or any other extranodal organ, skin, or bone marrow.

[48] A pharmaceutical composition for use in the treatment of cancer comprising a photosensitive substance, wherein the pharmaceutical composition is for use in a method comprising (1) irradiating blood collected from a subject with light, and (2) returning the light-irradiated blood to a vein of the subject, thereby enhancing immune response to cancer cells in the subject, wherein the photosensitive substance is administered to the subject prior to blood collection, or added to the blood collected from the subject prior to light irradiation.

[49] The pharmaceutical composition according to item 48, wherein the light has a level at which proportion of dead cells in cancer cells contained in the blood collected from the subject increases after the blood is returned to the subject.

[50] A pharmaceutical composition for use in the treatment of cancer comprising a photosensitive substance, wherein the pharmaceutical composition is for use in a method comprising (1) irradiating blood collected from a subject with light, and (2) returning the light-irradiated blood to a vein of the subject, wherein the photosensitive substance is administered to the subject prior to blood collection, or added to the blood collected from the subject prior to light irradiation, and the light has a level at which proportion of dead cells in cancer cells contained in the blood collected from the subject increases after the blood is returned to the subject.

[51] The pharmaceutical composition according to any one of items 48 to 50, wherein the light has an irradiation energy density of 2.5 to 300 J/cm$^2$.

[52] A pharmaceutical composition for use in the treatment of cancer comprising a photosensitive substance, wherein the pharmaceutical composition is for use in a method comprising (1) irradiating blood collected from a subject with light, and (2) returning the light-irradiated blood to a vein of the subject, wherein the photosensitive substance is administered to the subject prior to blood collection, or added to the blood collected from the subject prior to light irradiation, and the light has an irradiation energy density of 2.5 to 300 J/cm$^2$.

[53] The pharmaceutical composition according to any one of items 50 to 52, wherein the method enhances immune response to cancer cells in the subject by returning the light-irradiated blood to the subject.

[54] The pharmaceutical composition according to any one of items 48 to 53, wherein the method further comprises (1)' collecting blood from the subject prior to the irradiating of (1).

[55] The pharmaceutical composition according to item 54, wherein the method further comprises (1)" administering the photosensitive substance to the subject prior to the collecting of (1)'.

[56] The pharmaceutical composition according to item 54, wherein the method further comprises (1)"' adding the photosensitive substance to the blood collected from the subject after the collecting of (1)' prior to the irradiating of (1).

[57] The pharmaceutical composition according to any one of items 48 to 56, wherein the blood is collected and returned by an extracorporeal circulation device.

[58] The pharmaceutical composition according to any one of items 48 to 57, wherein the light has a wavelength of 200 to 2500 nm.

[59] The pharmaceutical composition according to item 58, wherein the light has a wavelength of 600 to 800 nm.

[60] The pharmaceutical composition according to any one of 48 to 59, wherein the light has an irradiation energy density of 10 to 300 J/cm$^2$.

[61] The pharmaceutical composition according to item 60, wherein the light has an irradiation energy density of about 100 J/cm$^2$.

[62] The pharmaceutical composition according to any one of items 48 to 61, wherein the photosensitive substance is an ALA compound.

[63] The pharmaceutical composition according to item 62, wherein the ALA compound is 5-aminolevulinic acid (5-ALA), a methyl ester or hexyl ester thereof, or a pharmaceutically acceptable salt thereof.

[64] The pharmaceutical composition according to item 63, wherein the ALA compound is 5-ALA or a pharmaceutically acceptable salt thereof.

[65] The pharmaceutical composition according to item 64, wherein 5-ALA or a pharmaceutically acceptable salt thereof is administered to the subject at a dose of 1 mg to 100 mg/kg.

[66] The pharmaceutical composition according to item 64, wherein 5-ALA or a pharmaceutically acceptable salt thereof is added to the blood collected from the subject at 0.01 mmol to 10 mmol/L.

[67] The pharmaceutical composition according to any one of items 48 to 66, wherein the cancer is a blood cancer.

[68] The pharmaceutical composition according to item 67, wherein the blood cancer is adult T-cell leukemia (ATL), acute myeloid leukemia (AML), acute lymphocytic leukemia (ALL), chronic myeloid leukemia (CML), or chronic lymphocytic leukemia (CLL).

[69] The pharmaceutical composition according to item 68, wherein the blood cancer is ATL.

[70] The pharmaceutical composition according to any one of items 48 to 66, wherein the cancer is a solid cancer.

[71] The pharmaceutical composition according to any one of items 48 to 70, wherein the pharmaceutical composition is for use in the treatment of a lesion of peripheral blood, lymph node, spleen, liver or any other extranodal organ, skin, or bone marrow.

[72] The pharmaceutical composition according to any one of items 48 to 70, wherein the pharmaceutical composition is for use in the prevention or treatment of cancer metastasis.

[73] The pharmaceutical composition according to item 72, wherein the cancer metastasis is a lesion of peripheral blood, lymph node, spleen, liver or any other extranodal organ, skin, or bone marrow.

[74] A method for treating cancer, the method comprising (1) irradiating blood collected from a subject with light, and (2) returning the light-irradiated blood to a vein of the subject, thereby enhancing immune response to cancer cells in the subject, wherein a photosensitive substance is administered to the subject prior to blood collection, or added to the blood collected from the subject prior to light irradiation.

[75] The method according to item 74, wherein the light has a level at which proportion of dead cells in cancer cells contained in the blood collected from the subject increases after the blood is returned to the subject.

[76] A method for treating cancer, the method comprising
(1) irradiating blood collected from a subject with light, and
(2) returning the light-irradiated blood to a vein of the subject,
wherein a photosensitive substance is administered to the subject prior to blood collection, or added to the blood collected from the subject prior to light irradiation, and
the light has a level at which proportion of dead cells in cancer cells contained in the blood collected from the subject increases after the blood is returned to the subject.

[77] The method according to any one of items 74 to 76, wherein the light has an irradiation energy density of 2.5 to 300 $J/cm^2$.

[78] A method for treating cancer, the method comprising
(1) irradiating blood collected from a subject with light, and
(2) returning the light-irradiated blood to a vein of the subject,
wherein a photosensitive substance is administered to the subject prior to blood collection, or added to the blood collected from the subject prior to light irradiation, and
the light has an irradiation energy density of 2.5 to 300 $J/cm^2$.

[79] The method according to any one of items 76 to 78, wherein the method enhances immune response to cancer cells in the subject by returning the light-irradiated blood to the subject.

[80] The method according to any one of items 74 to 79, further comprising
(1)' collecting blood from the subject prior to the irradiating of (1).

[81] The method according to item 80, further comprising
(1)" administering the photosensitive substance to the subject prior to the collecting of (1)'.

[82] The method according to item 80, further comprising
(1)'" adding the photosensitive substance to the blood collected from the subject after the collecting of (1)' prior to the irradiating of (1).

[83] The method according to any of items 74 to 82, wherein the blood is collected and returned by an extracorporeal circulation device.

[84] The method according to any one of items 74 to 83, wherein the light has a wavelength of 200 to 2500 nm.

[85] The method according to item 84, wherein the light has a wavelength of 600 to 800 nm.

[86] The method according to any one of items 74 to 85, wherein the light has an irradiation energy density of 10 to 300 $J/cm^2$.

[87] The method according to item 86, wherein the light has an irradiation energy density of about 100 $J/cm^2$.

[88] The method according to any one of items 74 to 87, wherein the photosensitive substance is an ALA compound.

[89] The method according to item 88, wherein the ALA compound is 5-aminolevulinic acid (5-ALA), a methyl ester or hexyl ester thereof, or a pharmaceutically acceptable salt thereof.

[90] The method according to item 89, wherein the ALA compound is 5-ALA or a pharmaceutically acceptable salt thereof.

[91] The method according to item 90, wherein 5-ALA or a pharmaceutically acceptable salt thereof is administered to the subject at a dose of 1 mg to 100 mg/kg.

[92] The method according to item 90, wherein 5-ALA or a pharmaceutically acceptable salt thereof is added to the blood collected from the subject at 0.01 mmol to 10 mmol/L.

[93] The method according to any one of items 74 to 92, wherein the cancer is a blood cancer.

[94] The method according to item 93, wherein the blood cancer is adult T-cell leukemia (ATL), acute myeloid leukemia (AML), acute lymphocytic leukemia (ALL), chronic myeloid leukemia (CML), or chronic lymphocytic leukemia (CLL).

[95] The method according to item 94, wherein the blood cancer is ATL.

[96] The method according to any one of items 74 to 92, wherein the cancer is a solid cancer.

[97] The method according to any one of items 74 to 96, wherein the treating cancer is treating a lesion of peripheral blood, lymph node, spleen, liver or any other extranodal organ, skin, or bone marrow.

[98] The method according to any one of items 74 to 96, wherein the treating cancer is preventing or treating cancer metastasis.

[99] The method according to item 98, wherein the cancer metastasis is a lesion of peripheral blood, lymph node, spleen, liver or any other extranodal organ, skin, or bone marrow.

[100] A system for use in the prevention or treatment of cancer metastasis, the system comprising
an extracorporeal circulation device comprising a blood circuit and a blood pump to collect and return blood of a subject, and
a light irradiation device to irradiate the blood circuit with light,
wherein a photosensitive substance is administered to the subject prior to blood collection, or added to blood collected from the subject prior to light irradiation, and
the system prevents development of a metastatic lesion or treats a metastatic lesion by returning the blood collected from the subject and irradiated with light to the subject.

[101] The system according to item 100, wherein the light has a level at which proportion of dead cells in cancer cells contained in the blood collected from the subject increases after the blood is returned to the subject.

[102] A system for use in the prevention or treatment of cancer metastasis, the system comprising
an extracorporeal circulation device comprising a blood circuit and a blood pump to collect and return blood of a subject, and
a light irradiation device to irradiate the blood circuit with light,
wherein a photosensitive substance is administered to the subject prior to blood collection, or added to blood collected from the subject prior to light irradiation, the blood collected from the subject and irradiated with light is returned to the subject, and the light has a level at which proportion of dead cells in cancer cells contained in the blood collected from the subject increases after the blood is returned to the subject.

[103] The system according to any one of items 100 to 102, wherein the light has an irradiation energy density of 2.5 to 300 J/cm$^2$.

[104] A system for use in the prevention or treatment of cancer metastasis, the system comprising an extracorporeal circulation device comprising a blood circuit and a blood pump to collect and return blood of a subject, and a light irradiation device to irradiate the blood circuit with light, wherein a photosensitive substance is administered to the subject prior to blood collection, or added to blood collected from the subject prior to light irradiation, the blood collected from the subject and irradiated with light is returned to the subject, and the light has an irradiation energy density of 2.5 to 300 J/cm$^2$.

[105] The system according to any one of items 100 to 104, wherein the system enhances immune response to cancer cells in the subject by returning the blood collected from the subject and irradiated with the light to the subject.

[106] The system according to any one of items 100 to 105, wherein the photosensitive substance is administered to the subject prior to blood collection.

[107] The system according to any one of items 100 to 106, further comprising the photosensitive substance.

[108] The system according to any one of items 100 to 107, wherein the light has a wavelength of 200 to 2500 nm.

[109] The system according to item 108, wherein the light has a wavelength of 600 to 800 nm.

[110] The system according to any one of items 100 to 109, wherein the light has an irradiation energy density of 10 to 300 J/cm$^2$.

[111] The system according to item 110, wherein the light has an irradiation energy density of about 100 J/cm$^2$.

[112] The system according to any one of items 100 to 111, wherein the photosensitive substance is an ALA compound.

[113] The system according to item 112, wherein the ALA compound is 5-aminolevulinic acid (5-ALA), a methyl ester or hexyl ester thereof, or a pharmaceutically acceptable salt thereof.

[114] The system according to item 113, wherein the ALA compound is 5-ALA or a pharmaceutically acceptable salt thereof.

[115] The system according to item 114, wherein 5-ALA or a pharmaceutically acceptable salt thereof is administered to the subject at a dose of 1 mg to 100 mg/kg.

[116] The system according to item 114, wherein 5-ALA or a pharmaceutically acceptable salt thereof is added to the blood collected from the subject at 0.01 mmol to 10 mmol/L.

[117] The system according to any one of items 100 to 116, wherein the cancer is a blood cancer.

[118] The system according to item 117, wherein the blood cancer is adult T-cell leukemia (ATL), acute myeloid leukemia (AML), acute lymphocytic leukemia (ALL), chronic myeloid leukemia (CML), or chronic lymphocytic leukemia (CLL).

[119] The system according to item 118, wherein the blood cancer is ATL.

[120] The system according to any one of items 100 to 116, wherein the cancer is a solid cancer.

[121] The system according to any of items 100 to 120, wherein the cancer metastasis a lesion of peripheral blood, lymph node, spleen, liver or any other extranodal organ, skin, or bone marrow.

[122] A method of preparing blood for use in the treatment of cancer, the method comprising adding a photosensitive substance to blood collected from a subject, and irradiating the blood to which the photosensitive substance is added with light, wherein the light-irradiated blood is to be administered to a vein of the subject.

[123] The method according to item 122, wherein the light-irradiated blood is capable of enhancing immune response to cancer cells in the subject.

[124] The method according to item 122 or 123, wherein the light has a wavelength of 200 to 2500 nm.

[125] The method according to item 124, wherein the light has a wavelength of 600 to 800 nm.

[126] The method according to any one of items 122 to 125, wherein the light has a level at which proportion of dead cells in cancer cells contained in the blood collected from the subject increases after the blood is returned to the subject.

[127] The method according to any one of items 122 to 126, wherein the light has an irradiation energy density of 2.5 to 300 J/cm$^2$.

[128] The method according to any one of items 122 to 127, wherein the light has an irradiation energy density of 10 to 300 J/cm$^2$.

[129] The method according to item 128, wherein the light has an irradiation energy density of about 100 J/cm$^2$.

[130] The method according to any one of items 122 to 129, wherein the photosensitive substance is an ALA compound.

[131] The method according to item 130, wherein the ALA compound is 5-aminolevulinic acid (5-ALA), a methyl ester or hexyl ester thereof, or a pharmaceutically acceptable salt thereof.

[132] The method according to item 131, wherein the ALA compound is 5-ALA or a pharmaceutically acceptable salt thereof.

[133] The method according to item 132, wherein 5-ALA or a pharmaceutically acceptable salt thereof is added to the blood collected from the subject at 0.01 mmol to 10 mmol/L.

[134] The method according to any one of items 122 to 133, wherein the cancer is a blood cancer.

[135] The method according to items 134, wherein the blood cancer is adult T-cell leukemia (ATL), acute myeloid leukemia (AML), acute lymphocytic leukemia (ALL), chronic myeloid leukemia (CML), or chronic lymphocytic leukemia (CLL).

[136] The method according to item 135, wherein the blood cancer is ATL.

[137] The method according to any one of items 122 to 133, wherein the cancer is a solid cancer.

[138] The method according to any one of items 122 to 137, wherein the blood is for use in the treatment of a lesion of peripheral blood, lymph node, spleen, liver or any other extranodal organ, skin, or bone marrow.

[139] The method according to any one of items 122 to 137, wherein the blood is for use in the prevention or treatment of cancer metastasis.

[140] The method according to item 139, wherein the cancer metastasis is a lesion of peripheral blood, lymph node, spleen, liver or any other extranodal organ, skin, or bone marrow.

[141] A method of preparing blood for use in the prevention or treatment of cancer metastasis, the method comprising adding a photosensitive substance to blood collected from a subject, and irradiating the blood to which the photosensitive substance is added with light, wherein the light-irradiated blood is to be administered to a vein of the subject.

[142] The method according to item 141, wherein the light-irradiated blood is capable of enhancing immune response to cancer cells in the subject.

[143] The method according to item 141 or 142, wherein the light has a wavelength of 200 to 2500 nm.

[144] The method according to item 143, wherein the light has a wavelength of 600 to 800 nm.

[145] The method according to any one of items 141 to 144, wherein the light has a level at which proportion of dead cells in cancer cells contained in the blood collected from the subject increases after the blood is returned to the subject.

[146] The method according to any one of items 141 to 145, wherein the light has an irradiation energy density of 2.5 to 300 J/cm$^2$.

[147] The method according to any one of items 141 to 146, wherein the light has an irradiation energy density of 10 to 300 J/cm$^2$.

[148] The method according to item 147, wherein the light has an irradiation energy density of about 100 J/cm$^2$.

[149] The method according to any one of items 141 to 148, wherein the photosensitive substance is an ALA compound.

[150] The method according to item 149, wherein the ALA compound is 5-aminolevulinic acid (5-ALA), a methyl ester or hexyl ester thereof, or a pharmaceutically acceptable salt thereof.

[151] The method according to item 150, wherein the ALA compound is 5-ALA or a pharmaceutically acceptable salt thereof.

[152] The method according to item 151, wherein 5-ALA or a pharmaceutically acceptable salt thereof is added to the blood collected from the subject at 0.01 mmol to 10 mmol/L.

[153] The method according to any one of items 141 to 152, wherein the cancer is a blood cancer.

[154] The method according to item 153, wherein the blood cancer is adult T-cell leukemia (ATL), acute myeloid leukemia (AML), acute lymphocytic leukemia (ALL), chronic myeloid leukemia (CML), or chronic lymphocytic leukemia (CLL).

[155] The method according to item 154, wherein the blood cancer is ATL.

[156] The method according to any one of items 141 to 152, wherein the cancer is a solid cancer.

[157] The method according to any one of items 141 to 156, wherein the cancer metastasis is a lesion of peripheral blood, lymph node, spleen, liver or any other extranodal organ, skin, or bone marrow.

[158] A photosensitive substance for use in the treatment of cancer, wherein the photosensitive substance is for use in the method according to any one of items 74 to 99.

[159] Use of a photosensitive substance for the manufacture of a medicament for use in the treatment of cancer, wherein the medicament is for use in the method according to any one of items 74 to 99.

[160] A method of controlling operation of a system for use in the treatment of cancer, the system comprising an extracorporeal circulation device comprising a blood circuit and a blood pump to collect and return blood of a subject, and a light irradiation device to irradiate the blood circuit with light, wherein a photosensitive substance has been administered to the subject prior to blood collection, or added to blood collected from the subject prior to light irradiation, the method comprising controlling operation of the system so that the light irradiation device emits light having an irradiation energy density at which proportion of living cells in a cell suspension irradiated with the light 24 hours after irradiation is lower than that immediately after irradiation, wherein the cell suspension is prepared by culturing cancer cells in a medium containing 0.5 mM 5-ALA for 4 hours, collecting the cancer cells, and suspending the collected cells with an erythrocyte solution to provide a cell suspension of $2\times10^7$ cells/mL.

[161] The method according to item 160, wherein the light emitted from the light irradiation device has an irradiation energy density at which the proportion of living cells in the cell suspension irradiated with the light immediately after irradiation is 8% or more, and the proportion 24 hours after irradiation is 2% or more lower than the proportion immediately after irradiation.

[162] The method according to item 160 or 161, wherein the light emitted from the light irradiation device has an irradiation energy density at which the proportion of living cells in the cell suspension irradiated with the light immediately after irradiation is 8% or more, and the proportion 24 hours after irradiation is 2% or more lower than the proportion immediately after irradiation, and proportion of apoptotic or necrotic cells 24 hours after irradiation is 2% or more higher than that immediately after irradiation.

[163] The method according to any one of items 160 to 162, wherein the light emitted from the light irradiation device has a wavelength of 630 nm.

The present invention will be further described with reference to the following examples, although it is not limited to these examples in any sense.

EXAMPLES

Example 1

1. Methods

Intravenous Administration of PDT-Treated C6 Cells

Rat glioma cell line C6 cells (ATCC) were cultured in 2.5% FBS/F-12K medium (Thermo Fisher Scientific) supplemented with aminolevulinic acid (5-ALA) (Sigma-Aldrich) to a final concentration of 1 mM in a 5% $CO_2$ incubator at 37° C. for 24 hours. After the culture, the cells were washed with PBS and treated with 0.25% trypsin-EDTA solution (Thermo Fisher Scientific) and adjusted to $2\times10^7$ cells/mL with PBS. The cell suspension thus prepared was injected into a Tygon tube (inner diameter: 0.79 mm, Saint-Gobain), wrapped around a light irradiator (Otsuka Electronics Co., Ltd.), and irradiated with light having a wavelength of 630 nm. The irradiation was performed under the following two irradiation conditions (PDT-1 and PDT-2).

PDT-1

Illuminance: 264.2 mW/cm$^2$

Duration: 20 minutes

Irradiation energy density: 317.0 J/cm$^2$

PDT-2

Illuminance: 124.5 mW/cm$^2$ (1st round)

91.4 mW/cm$^2$ (2nd and 3rd rounds*)

Duration: 1 minute

Irradiation energy density: 7.5 J/cm$^2$ (1st round)

5.5 J/cm$^2$ (2nd and 3rd rounds*)

Judging from the rate of dead cells at the 1st round, the illuminance was adjusted to be weak.

The treated cells of each irradiation condition were pooled separately and the irradiation was repeated until the required dose was obtained. Under isoflurane (Pfizer) anesthesia, the PDT-treated cells were administered to F344 rats (8 week-old at the start of study, male, Charles River Laboratories Japan Inc.) at 0.5 mL (corresponding to $1\times10^7$ cells) per animal from the tail vein (3 animals per group). As a comparative control, 0.5 mL of PBS alone was intravenously administered (3 animals). Intravenous administration of these PDT-treated cells was performed a total of 3 times (Day−21, −14, −1).

Rate of Dead Cells in PDT-Treated C6 Cells

The PDT-treated C6 cells were stained with FITC-labeled Annexin V and PI using the FITC Annexin V Apoptosis Detection Kit I (BD). After that, the rate of dead cells was analyzed with a flow cytometer (FACSCalibur, BD).

Subcutaneous Transplantation of C6 Cells (Preparation of Cancer-Bearing Rats)

On the day after the 3rd intravenous administration of PDT-treated cells (Day 0), C6 cells were washed with PBS, treated with 0.25% trypsin-EDTA solution, and adjusted to $2\times10^7$ cells/mL with PBS. Under isoflurane anesthesia, the cells were subcutaneously transplanted into the left abdomen of F344 rats at 0.5 mL ($1\times10^7$ cells) per animal.

Calculation of Tumor Volume

On the 3rd, 6th, 8th and 10th days after preparation of the cancer-bearing rats (Day 3, 6, 8, 10), the major axis and the minor axis of the tumor were measured by using a caliper, and the tumor volume was calculated according to the following formula.

$$\text{Tumor volume}=\tfrac{1}{6}\times\pi\times\text{major axis}\times\text{minor axis}^2$$

Measurement of Tumor Infiltrating $CD8^+$ T Cells

On the 10th day (Day 10), the rats were euthanized by collecting all blood under isoflurane anesthesia, and the tumors were removed. The removed tumors were fixed with formalin (Wako Pure Chemical Industries, Ltd.), and tissue section specimens were prepared and immunohistochemical staining (staining of $CD8^+$ T cells) was performed. After the staining, CD8+ T cells in 3 fields were randomly measured at a magnification of 400 times.

IFN-γ Production by Spleen Cells

The spleens were also removed from the euthanized rats, cut into small pieces, and squeezed with gauze to provide spleen cells. The collected spleen cells were washed, and then separated into mononuclear cells by using a solution for specific density separation (Lympholyte-Rat, Cedarlane).

The cells were washed again and adjusted to $1\times10^6$ cells/mL with 10% FBS/RPMI1640 medium. Separately, C6 cells were washed with PBS, treated with 0.25% trypsin-EDTA solution, and adjusted to $1\times10^5$ cells/mL. Then, 100 μL of the spleen cells and 100 μL of the C6 cells were added to a 96-well flat bottom plate (Sumitomo Bakelite Co., Ltd.), and the cells were cultured in a 5% $CO_2$ incubator at 37° C. for 24 hours. The culture supernatant after the culture was collected, and the amount of IFN-γ was measured by ELISA (R & D Systems).

2. Results

Figure 2:
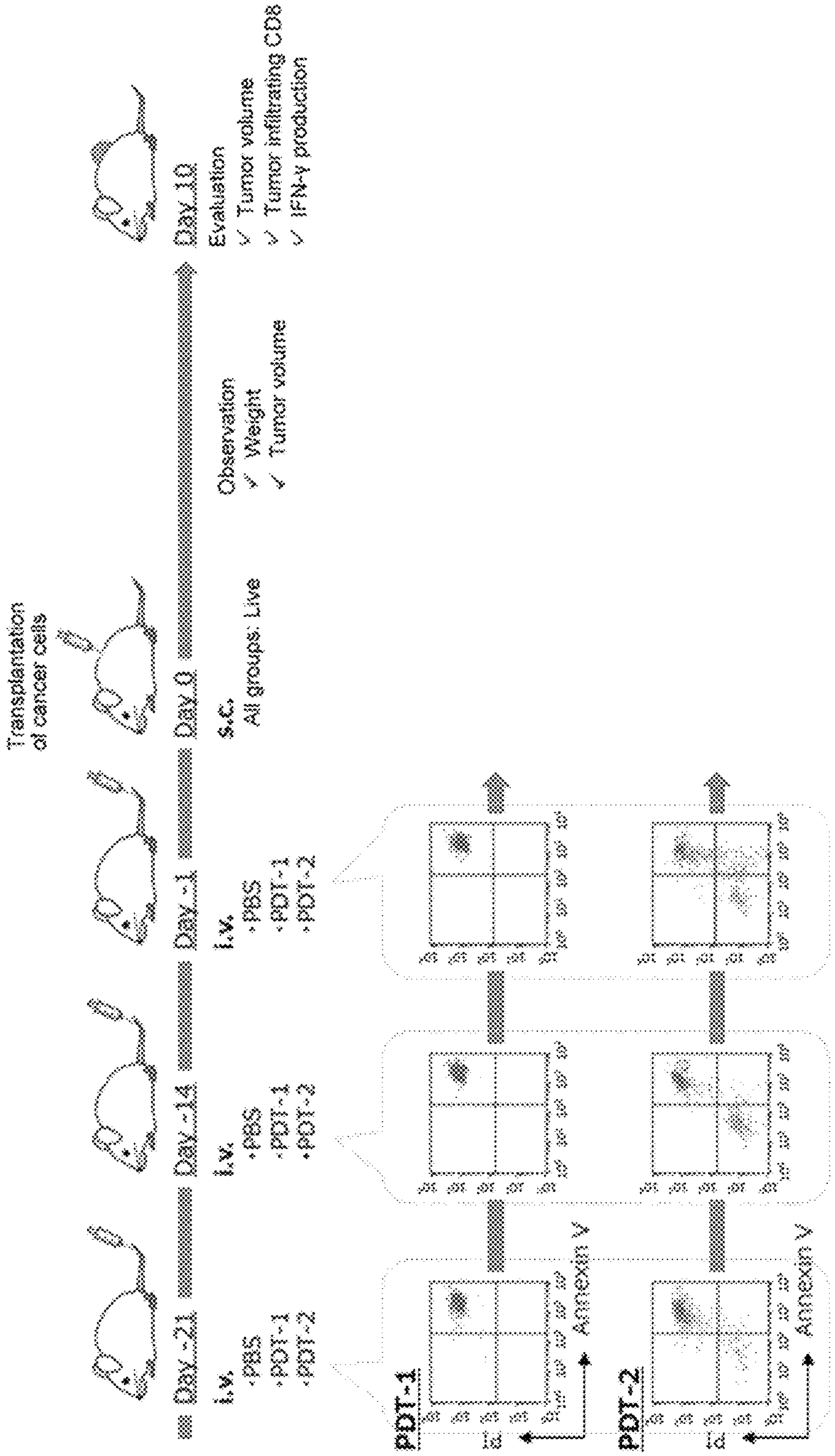
FIG. 2 shows the experimental protocol of the example.
Figure 3:
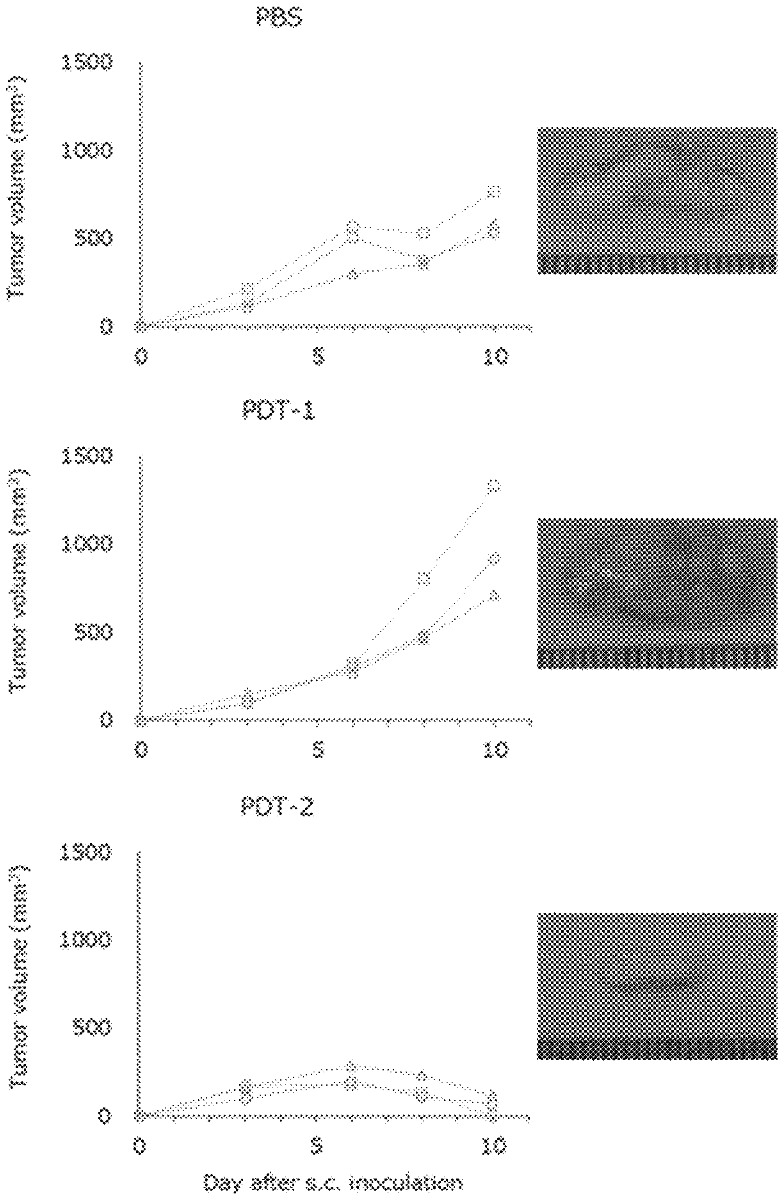
FIG. 3 shows the tumor volume of cancer-bearing rats (left) and the tumor tissues removed on the 10th day (right) after subcutaneous transplantation of C6 cells. In the left graph, the vertical axis shows the tumor volume (mm 3) and the horizontal axis shows the number of days after subcutaneous transplantation of C6 cells.

The protocol for this experiment is shown in FIG. 2. Immediately after irradiation, almost 100% of PDT-1-treated cells were Annexin V (+) and PI (+) necrotic cells (FIG. 2). In the PDT-2-treated cells, Annexin V (−) and PI (−) living cells are about 20%, and among dead cells, Annexin V (+) and PI (−) apoptotic cells and Annexin V (+) and PI (+) necrotic cells were mixed and Annexin V (+) and PI (−) cells were about 5 to 20%, and then 24 hours after irradiation, almost all cells became Annexin V (+) and PI (+). FIG. 3 shows changes in tumor volume after subcutaneous transplantation of C6 cells in rats treated with PBS, PDT-1-treated cells, or PDT-2-treated cells prior to the subcutaneous transplantation. In the rats treated with PBS prior to subcutaneous transplantation of C6 cells, an increase in tumor volume was observed after the subcutaneous transplantation. In contrast, in the rats treated with PDT-2-treated cells, this increase in tumor volume was suppressed. Such suppression was not observed with administration of PDT-1-treated cells.

Figure 4:
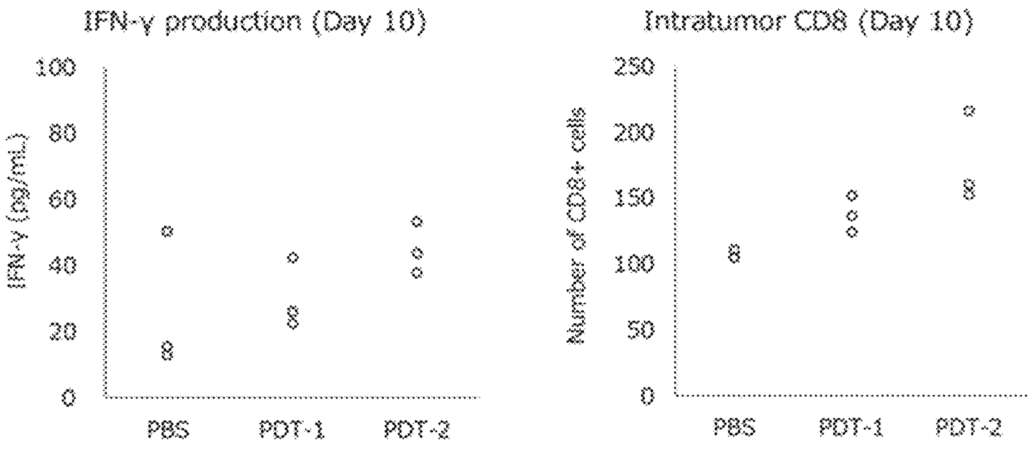
FIG. 4 shows IFN-γ production by spleen cells (left) and tumor-infiltrating $CD8^+$ T cells (right) in cancer-bearing rats.

IFN-γ production by tumor-infiltrating CD8+ T cells and spleen cells on the 10th day after subcutaneous transplantation of C6 cells (Day 10) was higher in the rats treated with PDT-2-treated cells than in the rats treated with PBS or PDT-1-treated cells (FIG. 4).

The above results indicate that proliferation of transplanted C6 cells was suppressed as a result of immunostimulation against C6 cells in rats treated with PDT-2-treated cells.

Example 2

1. Methods

Intravenous Administration of PDT-Treated C6 Cells

C6 cells were cultured in 2.5% FBS/F-12K medium supplemented with 5-ALA to a final concentration of 1 mM in a 5% $CO_2$ incubator at 37° C. for 24 hours. After the culture, the cells were removed with 0.25% trypsin-EDTA solution, and the collected cells were adjusted to $2\times10^7$ cells/mL with PBS. The cell suspension thus prepared was injected into a Tygon tube (inner diameter: 0.79 mm), wrapped around a light irradiator (Otsuka Electronics Co., Ltd.), and irradiated with light having a wavelength of 630 nm and an irradiation energy density of 7.5 J/cm$^2$ (illuminance of 124.5 mW/cm$^2$ for 1 minute). The treated cells were pooled and the irradiation was repeated until the required dose was obtained. The irradiated cells were divided into three equal parts, and one was administered to F344 rats (8 week-old at the start of study, male, Charles River Laboratories Japan Inc.) at 0.5 mL ($1\times10^7$ cells) per animal from the tail vein under isoflurane anesthesia (PDT iv group, 3 animals). Another one was centrifuged to remove its culture supernatant and adjusted to $2\times10^7$ cells/mL with PBS, and the cell suspension thus prepared was administered at 0.5 mL ($1\times10^7$ cells) per animal from the tail vein in the same manner as the PDT iv group (PDT-cell iv group, 3 animals). The cells of the remaining one of the three equal parts were suspended in 2.5% FBS/F-12K medium and cultured in a 5% $CO_2$ incubator at 37° C. for 24 hours, and then collected and adjusted to $2\times10^7$ cells/mL with PBS, and the cell suspension thus prepared was administered at 0.5 mL ($1\times10^7$ cells) per animal from the tail vein in the same manner as other groups (PDT/24 h-cell iv group, 3 animals). Intravenous administration of these PDT-treated cells was performed a total of 3 times (Day−15, −8, −1).

Intravenous Administration of C6 Cells Treated with an Anti-Cancer Agent

C6 cells were cultured in 2.5% FBS/F-12K medium supplemented with mitoxantrone dihydrochloride (MTX) (Sigma-Aldrich), doxorubicin hydrochloride (DOX) (Sigma-Aldrich) or epirubicin hydrochloride (EPI) (Sigma-Aldrich) to a final concentration of 20 μg/mL (MTX), 75 μg/mL (DOX), or 62.5 μg/mL (EPI), in a 5% $CO_2$ incubator at 37° C. for 48 hours. After the culture, the cells were removed with 0.25% trypsin-EDTA solution, and the collected cells were adjusted to $2\times10^7$ cells/mL with PBS. The cells treated with the anti-cancer agent were administered to F344 rats at 0.5 mL ($1\times10^7$ cells) per animal from the tail vein under isoflurane anesthesia (MTX-cell iv group, DOX-cell iv group and EPI-cell iv group, 3 animals in each group). Intravenous administration of these treated cells was performed a total of 3 times (Day−15, −8, −1).

Rate of Dead Cells in PDT-Treated or Anti-Cancer Agent-Treated C6 Cells

The PDT-treated or anti-cancer agent-treated C6 cells were stained with FITC-labeled Annexin V and PI by using the FITC Annexin V Apoptosis Detection Kit I. After that, the rate of dead cells was analyzed with a flow cytometer.

Subcutaneous Transplantation of C6 Cells (Preparation of Cancer-Bearing Rats)

On the day after the 3rd intravenous administration of PDT-treated cells or anti-cancer agent-treated cells (Day 0), untreated C6 cells were removed with 0.25% trypsin-EDTA solution, collected, and then adjusted to $2\times10^7$ cells/mL with PBS. Under isoflurane anesthesia, the cells were subcutaneously transplanted into the left abdomen of F344 rats at 0.5 mL ($1\times10^7$ cells) per animal.

Calculation of Tumor Volume

On the 4th, 6th, 8th and 10th days after preparation of the cancer-bearing rats (Day 4, 6, 8, 10), the major axis and the minor axis of the tumor were measured by using a caliper, and the tumor volume was calculated according to the following formula.

$$\text{Tumor volume} = \tfrac{1}{6}\times\pi\times\text{major axis}\times\text{minor axis}^2$$

Measurement of DAMPs (Damage-Associated Molecular Patterns)

The PDT-treated or anti-cancer agent-treated C6 cells were stained with an FITC-labeled anti-calreticulin antibody (Bioss) or an FITC-labeled isotype control (Bioss), and the fluorescence intensity of calreticulin was analyzed with a flow cytometer. Also, HMGB1 concentration in the supernatant obtained by centrifugation of the PDT-treated or anti-cancer agent-treated C6 cells was measured with the HMGB1 ELISA Kit II (Sinotest).

2. Results

Figure 5:
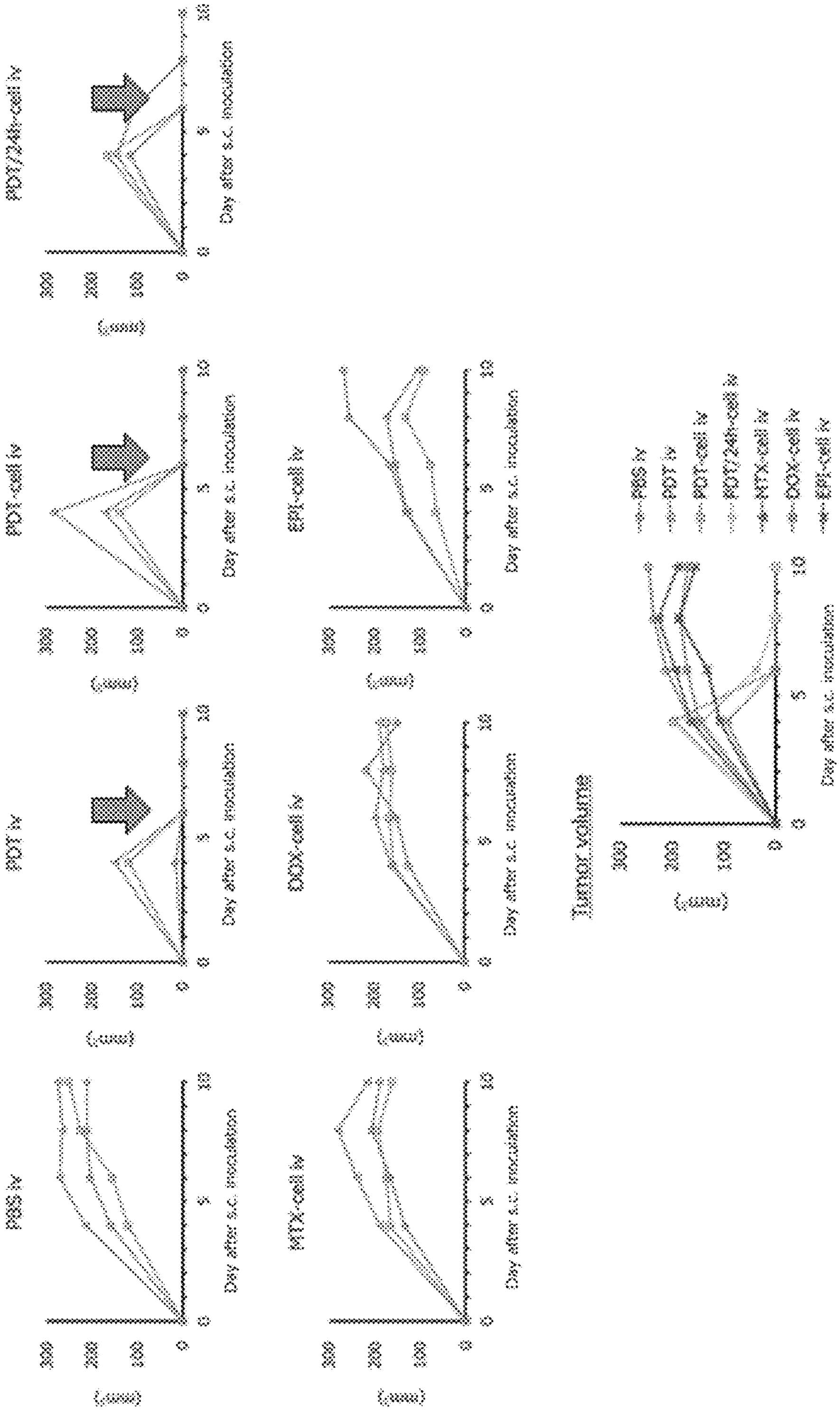
FIG. 5 shows the tumor volume of cancer-bearing rats after subcutaneous transplantation of C6 cells. The vertical axis shows the tumor volume (mm 3) and the horizontal axis shows the number of days after subcutaneous transplantation of C6 cells.
Figure 6:
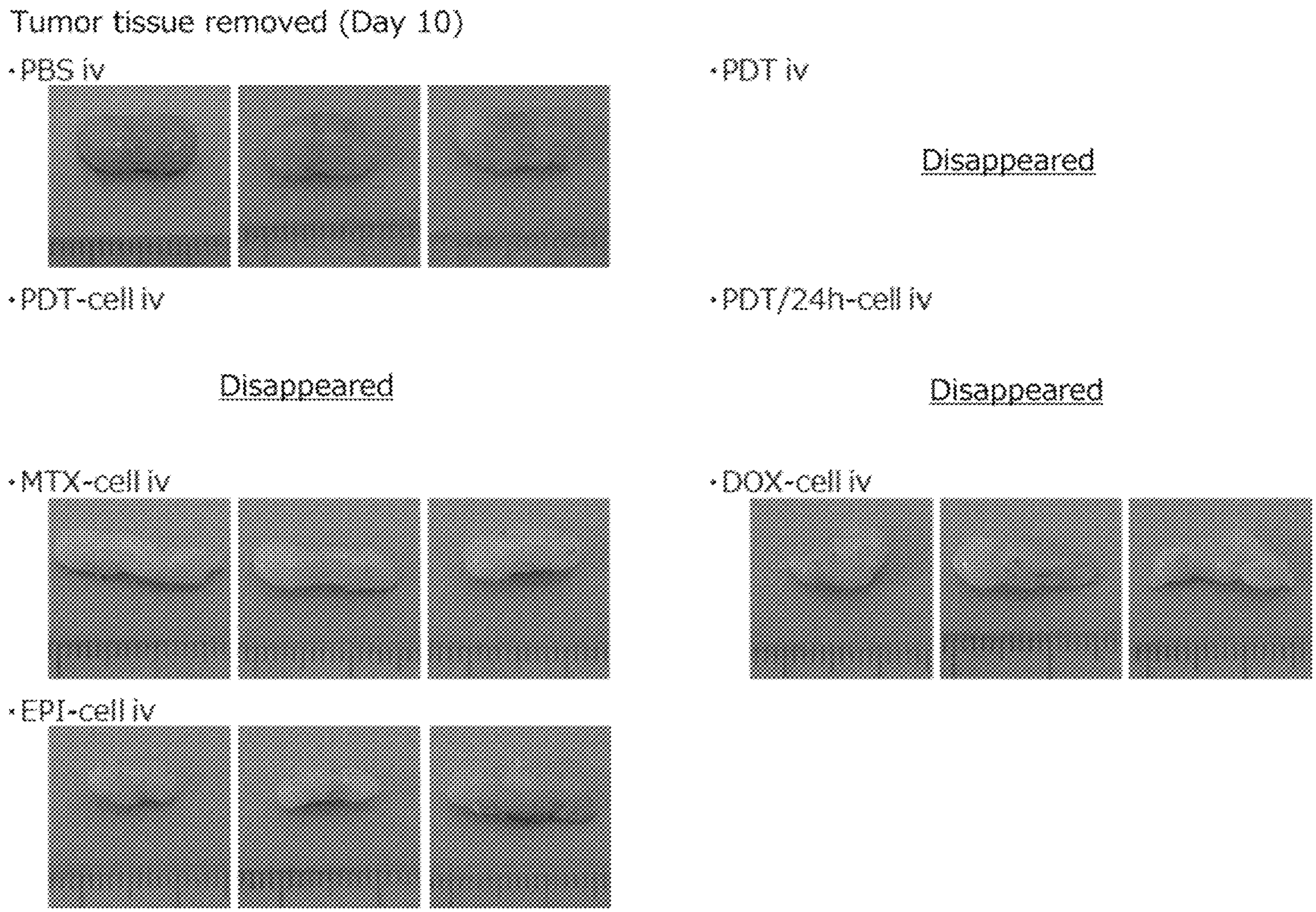
FIG. 6 shows the tumor tissues removed from cancer-bearing rats on the 10th day.
Figure 7:
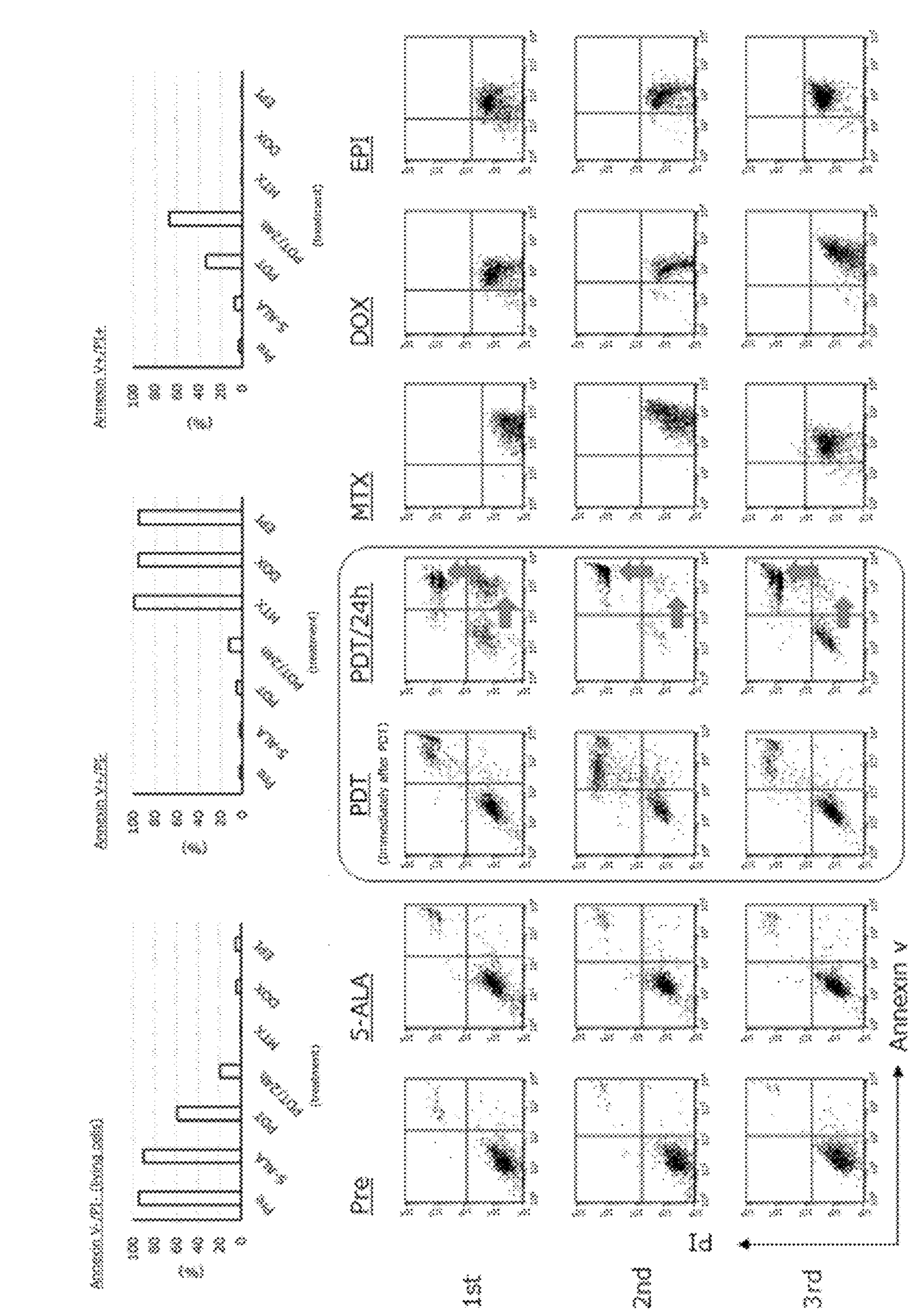
FIG. 7 shows the results of staining of PDT-treated cells and anti-cancer agent-treated cells with Annexin V and PI. Pre: untreated cells; 5-ALA: cells treated with 5-ALA but not treated with PDT; PDT: cells immediately after PDT treatment; PDT/24 h: cells cultured for 24 hours after PDT treatment; MTX, DOX, EPI: cells cultured for 48 hours after anti-cancer agent treatment.
Figure 8:
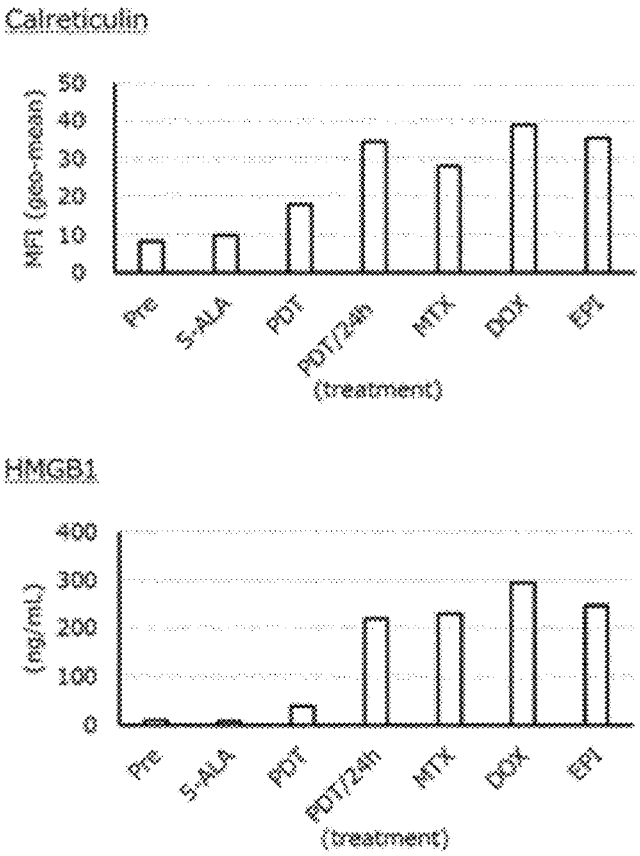
FIG. 8 shows calreticulin on the cell surface and HMGB1 in the supernatant of PDT-treated cells and anti-cancer agent-treated cells.

The changes in tumor volume after subcutaneous transplantation of C6 cells in PDT iv group, PDT-cell iv group, PDT/24 h-cell iv group, MTX-cell iv group, DOX-cell iv group, and EPI-cell iv group, as well as a group where PBS (0.5 mL) was intravenously administered as a control (PBS iv group) are shown in FIG. 5, and the tumor tissue removed 10 days after subcutaneous transplantation of C6 cells is shown in FIG. 6. An increase in tumor volume was observed in the PBS iv group, whereas this increase in tumor volume was suppressed in the PDT iv group, PDT-cell iv group, and PDT/24 h-cell iv group. In contrast, this suppression was not observed in the MTX-cell iv group, DOX-cell iv group, and EPI-cell iv group.

The anti-cancer agent-treated cells contained almost no living cells (Annexin V−/PI−), 1% in MTX-treated cells, 5% in DOX-treated cells, and 5% in EPI-treated cells. In contrast, the PDT-treated cells contained about 20-60% of living cells immediately after the treatment and even after 24-hour culture. Immediately after irradiation, dead cells in PDT-treated cells contained both apoptotic cells (Annexin V+/PI−) and necrotic cells (Annexin V+/PI+), and the proportion of living cells decreased while that of apoptotic and necrotic cells increased within 24 hours after the treatment, indicating that the living cells gradually died.

Calreticulin expression and HMGB1 release in PDT-treated cells were not high immediately after the PDT treatment, but increased 24 hours after the treatment. In the anti-cancer agent-treated cells, both calreticulin expression and HMGB1 release were strongly induced.

The results are summarized in Table 1. It was demonstrated that intravenous administration of PDT-treated cells induced antitumor immunity. This effect was observed with cells immediately after PDT treatment and with cells after 24-hour culture, and also observed when the cells were administered without their culture supernatant. It was considered that PDT-treated cells gradually died, thereby causing expression and release of DAMPs in vivo and inducing antitumor immunity. In contrast, although MTX, DOX, and EPI had been reported to have immunostimulatory effects in subcutaneous administration, antitumor immunity was not induced by intravenous administration of cells treated with these agents.

TABLE 1

| Group | Cell surface calreticulin | Supernatant HMGB1 | Antitumor immunity* |
|---|---|---|---|
| PBS iv | − | − | − |
| PDT iv | + | + | + |
| PDT-cell iv | + | (+)* | + |
| PDT/24 h-cell iv | ++ | (++)* | + |
| MTX-cell iv | ++ | (++)* | − |
| DOX-cell iv | ++ | (++)* | − |
| EPI-cell iv | ++ | (++)* | − |

*The parentheses were given because the treated cells were intravenously administered without their supernatant, although HMGB1 release was confirmed by the treatment of PDT or an anti-cancer agent. The symbol "+" in the antitumor immunity column means that an increase in tumor volume was suppressed.

Example 3

1. Methods

C6 cells or human leukemia cell line TL-Oml cells were cultured in 2.5% FBS/F-12K medium (C6 cells) or 10% FBS/RPMI1640 (TL-Oml cells) supplemented with 5-ALA to a final concentration of 0.125 to 0.5 mM in a 5% $CO_2$ incubator at 37° C. for 4 hours. After the culture, the cells were removed with a 0.25% trypsin-EDTA solution, and the collected cells were adjusted to $2\times10^7$ cells/mL with an erythrocyte solution (a solution in which erythrocytes and PBS were mixed at a ratio of 45:55). The cell suspension thus prepared was injected into a Tygon tube (inner diameter: 0.79 mm), wrapped around a light irradiator, and irradiated with light having a wavelength of 630 nm so that the irradiation energy density was 0.5 to 500 J/cm$^2$. After the irradiation, an ammonium chloride solution was added to the cell suspension to hemolyze the erythrocytes. Cells before the PDT treatment, after the PDT treatment, and after 24-hour culture were stained with the FITC Annexin V Apoptosis Detection Kit I and the rate of dead cells was analyzed with a flow cytometer.

2. Results

The results are summarized in Tables 2 and 3.

The results shown in Tables 2 and 3 were studied to determine conditions under which PDT-treated cells gradually died. We focused on the results of final concentrations of 0.25 mM and 0.5 mM, which were considered to provide a sufficient amount of 5-ALA to the cells from the changes in the irradiation energy density and the rate of living cells. Considering the results of Examples 1 and 2, we studied whether the irradiation energy density resulted in that proportion of living cells immediately after irradiation was 8%

TABLE 2

C6 cells

| | | Irradiation energy density (J/cm$^2$) | 20 | 50 | 100 | 400 | 500 |
|---|---|---|---|---|---|---|---|
| 5-ALA 0.125 (mM) | Immediately after irradiation | Annexin V–/PI– (%) | 97 | 95 | 95 | 93 | 82 |
| | | Annexin V+/PI– (%) | 1 | 1 | 1 | 1 | 0 |
| | | Annexin V+/PI+ (%) | 2 | 3 | 4 | 6 | 17 |
| | 24 hours after irradiation | Annexin V-/PI– (%) | 95 | 94 | 92 | 84 | 67 |
| | | Annexin V+/PI– (%) | 3 | 3 | 4 | 5 | 9 |
| | | Annexin V+/PI+ (%) | 2 | 3 | 4 | 10 | 27 |

| | | Irradiation energy density (J/cm$^2$) | 2.5 | 5 | 250 | 300 | 350 |
|---|---|---|---|---|---|---|---|
| 5-ALA 0.25 (mM) | Immediately after irradiation | Annexin V–/PI– (%) | 97 | 96 | 28 | 14 | 6 |
| | | Annexin V+/PI– (%) | 1 | 1 | 0 | 0 | 0 |
| | | Annexin V+/PI+ (%) | 2 | 3 | 70 | 83 | 91 |
| | 24 hours after irradiation | Annexin V–/PI– (%) | 93 | 88 | 23 | 10 | 2 |
| | | Annexin V+/PI– (%) | 5 | 8 | 8 | 4 | 1 |
| | | Annexin V+/PI+ (%) | 2 | 5 | 59 | 86 | 96 |

| | | Irradiation energy density (J/cm$^2$) | 0.5 | 1 | 2.5 | 100 | 350 | 400 | 500 |
|---|---|---|---|---|---|---|---|---|---|
| 5-ALA 0.5 (mM) | Immediately after irradiation | Annexin V–/PI– (%) | 95 | 96 | 94 | 15 | 8 | 5 | 2 |
| | | Annexin V+/PI– (%) | 2 | 1 | 1 | 2 | 0 | 0 | 0 |
| | | Annexin V+/PI+ (%) | 3 | 3 | 4 | 81 | 90 | 94 | 97 |
| | 24 hours after irradiation | Annexin V–/PI– (%) | 95 | 95 | 92 | 8 | 3 | 1 | 1 |
| | | Annexin V+/PI– (%) | 3 | 3 | 4 | 6 | 4 | 2 | 2 |
| | | Annexin V+/PI+ (%) | 2 | 2 | 4 | 86 | 92 | 96 | 98 |

TABLE 3

TL-Om1 cells

| | | Irradiation energy density (J/cm$^2$) | 10 | 50 | 100 | 200 | 300 | 400 | 500 |
|---|---|---|---|---|---|---|---|---|---|
| 5-ALA 0.125 (mM) | Immediately after irradiation | Annexin V–/PI– (%) | 91 | 90 | 91 | 90 | 89 | 88 | 85 |
| | | Annexin V+/PI– (%) | 2 | 2 | 2 | 2 | 3 | 2 | 2 |
| | | Annexin V+/PI+ (%) | 6 | 8 | 7 | 7 | 8 | 9 | 11 |
| | 24 hours after irradiation | Annexin V–/PI– (%) | 91 | 90 | 89 | 89 | 86 | 80 | 53 |
| | | Annexin V+/PI– (%) | 4 | 4 | 5 | 4 | 4 | 8 | 14 |
| | | Annexin V+/PI+ (%) | 6 | 6 | 6 | 7 | 9 | 12 | 33 |

| | | Irradiation energy density (J/cm$^2$) | 1 | 2.5 | 5 | 10 | 50 | 100 | 200 | 300 | 400 | 500 |
|---|---|---|---|---|---|---|---|---|---|---|---|---|
| 5-ALA 0.25 (mM) | Immediately after irradiation | Annexin V–/PI– (%) | 88 | 89 | 88 | 90 | 87 | 85 | 82 | 82 | 77 | 63 |
| | | Annexin V+/PI– (%) | 4 | 4 | 4 | 4 | 4 | 4 | 5 | 4 | 4 | 3 |
| | | Annexin V+/PI+ (%) | 8 | 6 | 7 | 6 | 8 | 10 | 12 | 13 | 18 | 33 |
| | 24 hours after irradiation | Annexin V–/PI– (%) | 90 | 89 | 88 | 86 | 83 | 83 | 79 | 75 | 50 | 7 |
| | | Annexin V+/PI– (%) | 6 | 7 | 8 | 8 | 9 | 8 | 10 | 11 | 16 | 21 |
| | | Annexin V+/PI+ (%) | 4 | 4 | 4 | 6 | 9 | 10 | 11 | 14 | 34 | 72 |
| 5-ALA 0.5 (mM) | Immediately after irradiation | Annexin V–/PI– (%) | 89 | 92 | 90 | 89 | 83 | 80 | 78 | 72 | 61 | 30 |
| | | Annexin V+/PI– (%) | 3 | 2 | 3 | 3 | 3 | 3 | 3 | 3 | 3 | 2 |
| | | Annexin V+/PI+ (%) | 7 | 5 | 7 | 8 | 12 | 16 | 18 | 23 | 32 | 62 |
| | 24 hours after irradiation | Annexin V–/PI– (%) | 90 | 89 | 86 | 85 | 78 | 71 | 59 | 29 | 7 | 5 |
| | | Annexin V+/PI– (%) | 5 | 5 | 6 | 7 | 9 | 13 | 16 | 19 | 18 | 16 |
| | | Annexin V+/PI+ (%) | 4 | 5 | 8 | 8 | 12 | 15 | 24 | 52 | 75 | 80 |

or more, and proportion of living cells 24 hours after irradiation was 2% or more lower than that immediately after irradiation. Such irradiation energy densities for C6 cells and TL-0 ml cells were shown below. Under these conditions, proportion of apoptotic cells or necrotic cells 24 hours after irradiation was 2% or more higher than that immediately after irradiation.

TABLE 4

| | 0.25 mM | 0.5 mM |
|---|---|---|
| C6 cells | 2.5-300 J/cm$^2$ | 2.5-350 J/cm$^2$ |
| TL-0m1 cells | 10-500 J/cm$^2$ | 2.5-500 J/cm$^2$ |

The results of Examples 1 to 3 demonstrated that the irradiation energy density of 2.5 to 300 J/cm$^2$ was suitable, and in particular, 10 to 300 J/cm$^2$ was applicable regardless of the cell type.

The invention claimed is:

1. A method for preventing or treating cancer metastasis, the method comprising (1) irradiating blood collected from a subject with light, and (2) returning the light-irradiated blood to a vein of the subject, wherein a photosensitive substance is administered to the subject prior to blood collection, or added to the blood collected from the subject prior to light irradiation, the light has an irradiation energy density of 30 to 300 J/cm$^2$, the light has a wavelength of 600 to 800 nm, the photosensitive substance is an ALA compound, and the cancer is a blood cancer.

2. The method according to claim 1, wherein the method enhances immune response to cancer cells in the subject by returning the light-irradiated blood to the subject.

3. The method according to claim 1, further comprising (1)' collecting blood from the subject prior to the irradiating of (1).

4. The method according to claim 3, further comprising (1)" administering the photosensitive substance to the subject prior to the collecting of (1)'.

5. The method according to claim 4, further comprising (1)"' adding the photosensitive substance to the blood collected from the subject after the collecting of (1)' prior to the irradiating of (1).

6. The method according to claim 1, wherein the blood is collected and returned by an extracorporeal circulation device.

7. The method according to claim 1, wherein the light has an irradiation energy density of about 100 J/cm$^2$.

8. The method according to claim 1, wherein the ALA compound is 5-aminolevulinic acid (5-ALA), a methyl ester or hexyl ester thereof, or a pharmaceutically acceptable salt thereof.

9. The method according to claim 8, wherein the ALA compound is 5-ALA or a pharmaceutically acceptable salt thereof.

10. The method according to claim 9, wherein 5-ALA or a pharmaceutically acceptable salt thereof is administered to the subject at a dose of 1 mg to 100 mg/kg.

11. The method according to claim 9, wherein 5-ALA or a pharmaceutically acceptable salt thereof is added to the blood collected from the subject at 0.01 mmol to 10 mmol/L.

12. The method according to claim 1, wherein the blood cancer is adult T-cell leukemia (ATL), acute myeloid leukemia (AML), acute lymphocytic leukemia (ALL), chronic myeloid leukemia (CML), or chronic lymphocytic leukemia (CLL).

13. The method according to claim 12, wherein the blood cancer is ATL.

14. The method according to claim 1, wherein the cancer metastasis is a lesion of peripheral blood, lymph node, spleen, liver or any other extranodal organ, skin, or bone marrow.

15. The method of according to claim 1, wherein the light has an irradiation energy density at which proportion of living cells in a cell suspension irradiated with the light 24 hours after irradiation is lower than that immediately after irradiation, wherein the cell suspension is prepared by culturing cancer cells in a medium containing 0.5 mM 5-ALA for 4 hours, collecting the cancer cells, and suspending the collected cells with an erythrocyte solution to provide a cell suspension of $2\times10^7$ cells/mL.

16. The method according to claim 15, wherein the light has an irradiation energy density at which the proportion of living cells in the cell suspension irradiated with the light immediately after irradiation is 8% or more, and the proportion 24 hours after irradiation is 2% or more lower than the proportion immediately after irradiation.

17. The method according to claim 15, wherein the light has an irradiation energy density at which the proportion of living cells in the cell suspension irradiated with the light immediately after irradiation is 8% or more, and the proportion 24 hours after irradiation is 2% or more lower than the proportion immediately after irradiation, and proportion of apoptotic or necrotic cells 24 hours after irradiation is 2% or more higher than that immediately after irradiation.

18. The method according to claim 1, wherein the irradiation energy density is selected so that a proportion of living cells immediately after irradiation is 8% or more;

a proportion of living cells 24 hours after irradiation is at least 2% lower than immediately after irradiation; and a proportion of apoptotic or necrotic cells 24 hours after irradiation is at least 2% higher than immediately after irradiation.

19. A method for preventing or treating cancer metastasis, the method comprising (1) irradiating blood collected from a subject with light, and (2) returning the light-irradiated blood to a vein of the subject, wherein a photosensitive substance is administered to the subject prior to blood collection, or added to the blood collected from the subject prior to light irradiation, and the light has an irradiation energy density of 30 to 300 J/cm$^2$, and the irradiation energy density is selected so that a proportion of living cells immediately after irradiation is 8% or more;

a proportion of living cells 24 hours after irradiation is at least 2% lower than immediately after irradiation; and a proportion of apoptotic or necrotic cells 24 hours after irradiation is at least 2% higher than immediately after irradiation.

* * * * *